US008574551B2

(12) United States Patent
Rowe

(10) Patent No.: US 8,574,551 B2
(45) Date of Patent: Nov. 5, 2013

(54) COMPOSITIONS USEFUL FOR REDUCING NEPHROTOXICITY AND METHODS OF USE THEREOF

(75) Inventor: Vernon D. Rowe, Shawnee, KS (US)

(73) Assignee: Verrow Pharmaceuticals, Inc., Lenexa, KS (US)

( * ) Notice: Subject to any disclaimer, the term of this patent is extended or adjusted under 35 U.S.C. 154(b) by 0 days.

(21) Appl. No.: 13/592,510

(22) Filed: Aug. 23, 2012

(65) Prior Publication Data

US 2012/0321564 A1 Dec. 20, 2012

Related U.S. Application Data

(60) Division of application No. 12/641,708, filed on Dec. 18, 2009, now Pat. No. 8,277,779, which is a continuation of application No. 11/753,883, filed on May 25, 2007, now Pat. No. 7,658,913, which is a continuation-in-part of application No. 11/562,924, filed on Nov. 22, 2006, now abandoned.

(60) Provisional application No. 60/778,037, filed on Mar. 1, 2006, provisional application No. 60/740,142, filed on Nov. 28, 2005.

(51) Int. Cl.
    *A61K 49/04* (2006.01)
(52) U.S. Cl.
    USPC .......................................... 424/9.43; 424/9.4
(58) Field of Classification Search
    USPC ................................. 424/9.43, 9.4
    See application file for complete search history.

(56) References Cited

U.S. PATENT DOCUMENTS

| | | |
|---|---|---|
| 3,426,011 A | 2/1969 | Parmerter et al. |
| 4,247,535 A | 1/1981 | Lewis et al. |
| 4,654,325 A | 3/1987 | Selenke |
| 4,696,918 A | 9/1987 | Stoddart |
| 4,727,064 A | 2/1988 | Pitha |
| 4,877,778 A | 10/1989 | Carpenter et al. |
| 4,916,225 A | 4/1990 | Zhuk et al. |
| 5,134,127 A | 7/1992 | Stella et al. |
| 5,441,944 A | 8/1995 | Weisz et al. |
| 5,759,573 A | 6/1998 | Kim |
| 5,780,446 A | 7/1998 | Ramu |
| 6,060,597 A | 5/2000 | Tobe et al. |
| 6,077,871 A | 6/2000 | Campeta |
| 6,407,079 B1 | 6/2002 | Müller et al. |
| 6,586,476 B1 | 7/2003 | Stogniew et al. |
| 6,730,664 B1 | 5/2004 | Muggetti et al. |
| 6,903,100 B2 | 6/2005 | Rowe |
| 7,026,288 B2 | 4/2006 | Judice et al. |
| 7,067,483 B2 | 6/2006 | Judice et al. |
| 2003/0220294 A1 | 11/2003 | Wallace et al. |
| 2004/0048871 A1 | 3/2004 | Rowe |
| 2005/0234017 A1 | 10/2005 | Zeldis |

FOREIGN PATENT DOCUMENTS

| | | |
|---|---|---|
| CN | 14411680 A | 9/2003 |
| EP | 0 434 470 | 6/1991 |
| JP | 2001-501478 | 5/1989 |
| JP | 2004-235128 | 8/1992 |
| JP | 2001-516358 | 9/2001 |
| JP | 2006-345871 | 12/2006 |
| KR | 1020010084737 | 9/2001 |
| KR | 1020010093525 A | 10/2001 |
| WO | WO8200251 | 2/1982 |
| WO | WO 98/41227 | 9/1998 |
| WO | WO0102393 | 1/2001 |
| WO | WO 01/19338 | 3/2001 |
| WO | WO0119339 | 3/2001 |
| WO | WO0182971 | 11/2001 |
| WO | WO03053475 | 7/2003 |
| WO | WO 2005/084695 | 9/2005 |
| WO | WO2007062403 | 5/2007 |

OTHER PUBLICATIONS

Polly E. Kintzel and Robert T. Dorr, Anticancer drug renal toxicity and elimination: dosing guidelines for altered renal function Cancer Treatment Reviews (1995) 21, 33-64.
Ackland and Schilsky (1987) J. Clin. Oncol. 5(12):2017-31 "High-dose methotrexate: a critical reappraisal".
Aime et al. (1999) Chem. Eur. J. 5:1253-1260; Abstract "Contrast Agents for Magnetic Resonance Imaging: A Novel Route to Enhanced Relaxivities Based on the Interaction of Gd III Chelate with Poly-beta-cyclodextrins".
Arany and Safirstein (2003) Seminars in nephrotoxicity 23(5):460-4 "Cisplatin nephrotoxicity".
Brewster et al. (1992) International Journal of Pharmaceutics 79:289-299 "Effect of various cyclodextrins on solution stability and dissolution rate of doxorubicin hydrochloride".
Challa et al. (2005) AAPS PharmSciTech 6(2):E329-E357 "Cyclodextrins in Drug Delivery: an updated review".
Extended European Search Report mailed Jul. 16, 2010 for search completed Jun. 23, 2010 in European Patent Application No. 08756113.0.
Frijlink et al. (1991) Pharm. Res. 8(1):9-16 "The effect of parenterally administered cyclodextrins on cholesterol levels in the rat."
Goodman and Gilman's The Pharmacological Basis of Therapeutics (2001) Editors Hardman and Limbird, published by The McGraw-Hill Companies, Inc. pp. 54-56.
Hewlett (2004) Canadian Family Physician 50:709-711 "Nephrotoxic drugs".
Ikeguchi et al. (2000) Int. J. Cancer 88:474-478; Abstract "Cisplatin Combined With Prostaglandin El Chemotherapy in Rat Peritoneal Carcinomatosis".
International Search Report for PCT Application No. PCT/US08/64489, dated Sep. 3, 2008.
Kikuchi et al. (1990) Pharmaceutical Research 7(6):644-647 "Effect of Dextran Sulfate on Renal Accumulation of Gentamicin".

(Continued)

*Primary Examiner* — Scarlett Goon
(74) *Attorney, Agent, or Firm* — Akerman Senterfitt LLP

(57) ABSTRACT

The present invention provides compositions and methods to reduce renal damage caused by nephrotoxic drugs. The invention provides compositions comprising an anionically substituted cyclodextrin, a nephrotoxic drug and a pharmaceutically acceptable carrier, where the cyclodextrin is present in an amount effective for substantially inhibiting the nephrotoxic effect of the drug.

13 Claims, 14 Drawing Sheets

(56) References Cited

OTHER PUBLICATIONS

Loftsson and Brewster (1996) Journal of Pharmaceutical Sciences 85(10):1017-1025 "Pharmaceutical Applications of Cyclodextrins. 1. Drug Solubilization and Stabilization".
Loftsson et al. (2005) Expert Opin. Drug Deliv. 2(2):335-351 "Cyclodextrins in drug delivery".
Miller (2003) Radiology Rounds vol. 1 issue 5 "Minimizing Adverse Reactions to Contrast Agents".
Mosher and Thompson (2002) Encyclopedia of Pharmaceutical Technology pp. 531-558 "Complexation and Cyclodextrins".
Pattarino et al. (2005) J. Drug Del. Sci. Tech. 15(6):465-468 "Inclusion of methotrexate in alkyl-cyclodextrins: effects of host substitutents on the stability of complexes".
Perazella (1999) Am. J. Med. 106(4):459-65 "Crystal-induced acute renal failure".
Perrin et al. (1978) Res. Commun. Chem. Pathol. Pharmacol. 19(2):373-6 "beta-Cyclodextrin as an aid to peritoneal dialysis. Renal toxicity of beta-cyclodextrin in the rat."
Perry et al. (2006) Journal of Pharmaceutical Sciences 95(1):146-158 "The Binding Interaction of Synthetic Ozonide Antimalarials with Natural and Modified β-Cyclodextrins".
Rao and Stella (2003) Journal of Pharmaceutical Sciences 92(5):927-932 "When Can Cyclodextrins Be Considered for Solubilization Purposes?"
Sahani and Setty (2005) Contrast Media: New Agents, New Concepts. Imaging Economics. Retrieved online from http://www.imagingeconomics.com/issues/articles/2005-07_03.asp on Sep. 21, 2009.
Schaschke et al. (2000) Bioorg Med Chem Lett 10(7):677-80 "Beta-cyclodextrin/epoxysuccinyl peptide conjugates: a new drug targeting system for tumor cells".
Schornagel and McVie (1983) Cancer Treat Rev. 10(1):53-75 "The clinical pharmacology of methotrexate".
Singh et al. (1997) Pharm. Sciences 3:573-77 "Physicochemical and biological studies of inclusion complex of methotrexate with β-cyclodextrin".
Skarby et al. (2003) Cancer Chemother. Pharmacol. 51(4):311-20 "High-dose methotrexate: on the relationship of methotrexate elimination time vs renal function and serum methotrexate levels in 1164 courses in 264 Swedish children with acute lymphoblastic leukaemia (ALL)".
Stella et al. (1999) Advanced Drug Delivery Reviews 36:3-16 "Mechanisms of drug release from cyclodextrin complexes".
Supplementary European Search Report re: European Patent Application No. EP 06 84 6375, Apr. 26, 2011.
Uekama (2004) Chemical and Pharmaceutical Bulletin 52(8):900-915 "Design and Evaluation of Cyclodextrin-Based Drug Formulation".
Uekama et al. (1992) J. Pharm. Pharmacol. 45(8):745-7 "Protective effects of cyclodextrin sulphates against gentamicin-induced nephrotoxicity in the rat".
Wang et al. (1999) J. of Histochemistry & Cytochemistry 47(8):1057-62 "Immunocytochemical and In Situ Hybridization Studies of Gastrin After Cisplatin Treatment".
Wang and Song (Mar. 31, 2007) Materials Review 21:3(40-43) "Progress in Pharmaceutical Applications of a New Excipient Sulfobutyl-beta-Cyclodextrins".
Widemann et al. (1997) J. Clin. Oncol. 15(5):2125-34 "Carboxypeptidase-G2, thymidine, and leucovorin rescue in cancer patients with methotrexate-induced renal dysfunction".
Zia et al. (2001) Pharmaceutical Research 18(5):667-673 "Effect of Cyclodextrin Charge on Complexation of Neutral and Charged Substrates: Comparison of (SBE)7M-β-CD to HP-β-CD".
Barrett, Brendan J., "Contrast Nephrotoxicity" Journal of the American Society of Nephrology, 1994, 5:125-137.

COMPOSITIONS USEFUL FOR REDUCING NEPHROTOXICITY AND METHODS OF USE THEREOF

This application is a divisional of U.S. Ser. No. 12/641,708, filed Dec. 18, 2009, which is a continuation application of U.S. Ser. No. 11/753,883, filed May 25, 2007, now U.S. Pat. No. 7,655,913, which is a continuation-in-part application of U.S. Ser. No. 11/562,924, which was filed Nov. 22, 2006, now abandoned, and which claims the benefit of U.S. Provisional Application No. 60/778,037, filed Mar. 1, 2006, and U.S. Provisional Application No. 60/740,142, filed Nov. 28, 2005, the entire contents of each of which are incorporated herein by reference.

BACKGROUND OF THE INVENTION

Numerous drugs and other substances are known to be nephrotoxic and can cause renal failure through a variety of mechanisms including direct toxicity to the renal tubules, allergic interstitial nephritis, and crystallization of the drug within the renal tubules, which can lead to acute oliguric renal failure. Nephrotoxic drugs include anticancer agents such as cisplatin, methotrexate, and doxyrubicin, non-steroidal anti-inflammatories (NSAIDS), such as COX-2 inhibitors, antibiotics (e.g., aminoglycosides, amphotericin) antivirals (e.g., acyclovir, indinivir), acetylcholinesterase inhibitors, angiotensin II receptor blockers (ARBs), lithium and radiographic contrast media.

A need exists to reduce renal damage caused by nephrotoxic drugs.

SUMMARY OF THE INVENTION

The present invention provides compositions and methods to reduce renal damage caused by nephrotoxic drugs. The invention provides compositions comprising an anionically substituted oligosaccharide, a nephrotoxic drug and a pharmaceutically acceptable carrier, where the oligosaccharide is present in an amount effective for substantially inhibiting the nephrotoxic effect of the drug.

Also provided are compositions having reduced nephrotoxic effect comprising a pharmaceutically active compound having nephrotoxic effect and a polyanionic oligosaccharide where the oligosaccharide is present in an amount effective to substantially reduce the nephrotoxic effect of the pharmaceutically active compound.

Also disclosed herein are methods of reducing the nephrotoxic effect of a pharmaceutically active compound comprising contacting the compound with a polyanionic oligosaccharide. Additionally, methods are disclosed for inhibiting nephrotoxicity associated with a nephrotoxic drug, the method comprising administering a pharmaceutical composition comprising a cyclic polysaccharide sulfate, the nephrotoxic inducing drug and optionally a pharmaceutically acceptable carrier.

DETAILED DESCRIPTION OF THE INVENTION

Figure 1:
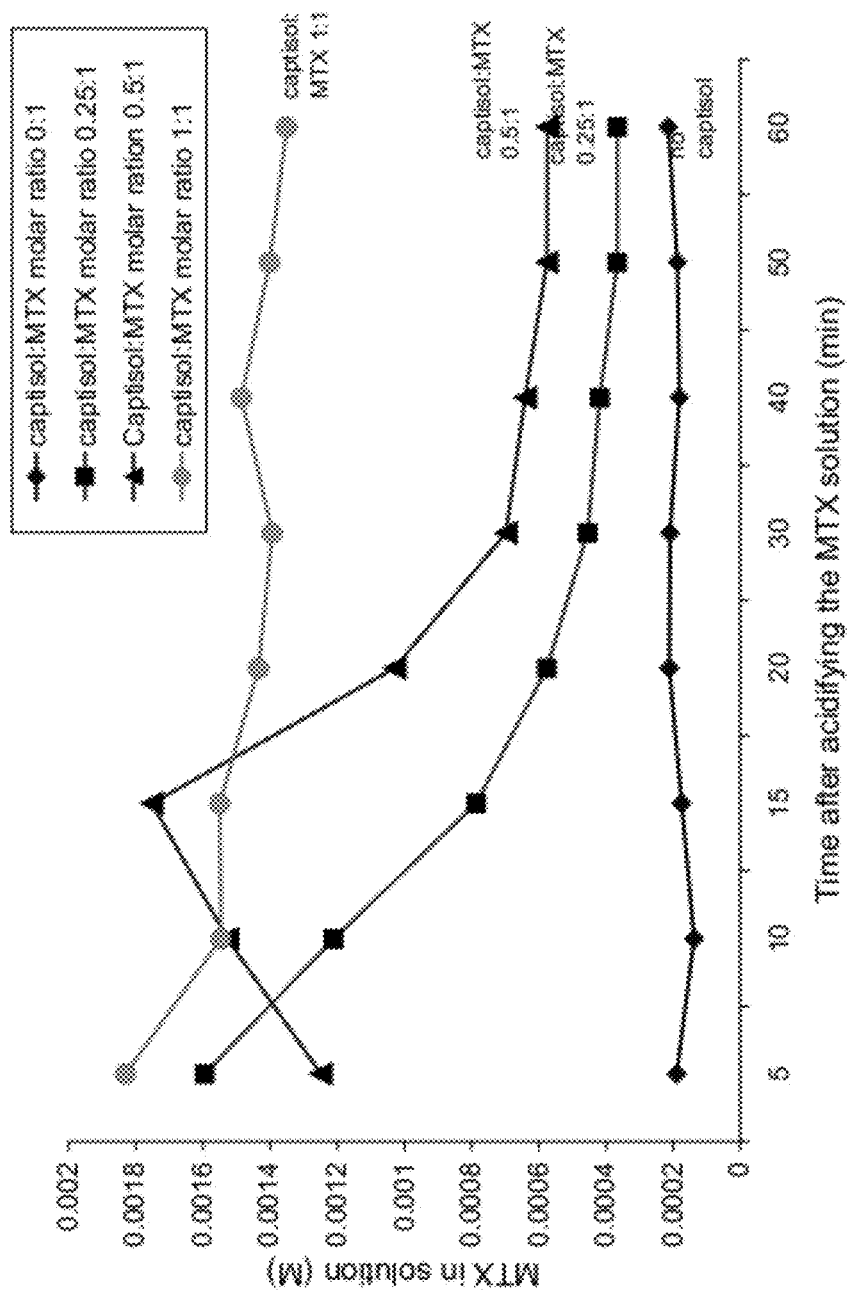
FIG. 1 shows solubility study results with methotrexate (MTX) and captisol in aqueous acidic solution.

The compositions of the present invention typically comprise an anionically substituted oligosaccharide, a nephrotoxic drug and typically a pharmaceutically acceptable carrier or other excipient commonly used in the art. The oligosaccharide is present in an amount effective to substantially inhibit the nephrotoxic effect of the drug. In one embodiment, the oligosaccharides are substituted with polar or charged moieties, such as cationic or anionic substituents. In one example, the anionically substituted oligosaccharide is a polyanionic oligosaccharide comprising a cyclodextrin having one or more anionic substituents selected from the group consisting of sulfonate, sulfate, carboxylate, phosphonate and phosphate. In another embodiment, the oligosaccharide is a cyclic polysaccharide sulfate, preferably an α, β or γ-cyclodextrin sulfate.

The present invention also provides compositions having reduced nephrotoxic effect comprising a pharmaceutically active compound having nephrotoxic inducing effect and a polyanionic oligosaccharide. Nephrotoxic as used herein means toxic or destructive to the kidney, or any of its components.

Substituted Oligosaccharides

Substituted oligosaccharides generally refer to oligosaccharides having at least one substituent per molecule, preferably a charged or polar substituent. The oligosaccharides are preferably saccharides of from about 5 to about 10 sugar units and have molecular weights, when unsubstituted, from about 650 to about 1300. Where the oligosaccharide is anionically substituted, it is generally preferred that the substituents be selected from the group consisting of sulfonate, sulfate, carboxylate, phosphonate and phosphate groups and combinations thereof. The substituents are preferably present in the molecule to an extent of from about 0.5 to about 3 substituents per sugar unit. Especially preferred compositions are those based on oligosaccharides having about 1 sulfonate substituent per sugar unit. Other preferred compositions are based on oligosaccharides having from about 2 to about 3 substituents per sugar unit, wherein the substituents comprise sulfate, sulfonate and/or phosphate substituents.

Oligosaccharides are chains of several sugar units such as glucose units, connected through glycosidic oxygen atoms. As used herein, the prefix "oligo" indicates an intermediate number of sugar or saccharide units, as compared to a monomeric sugar unit of one, or at most two as in sucrose, and a polysaccharide having twenty or more of sugar units and high molecular weight. While all such oligosaccharides are believed to be operable within the scope of the present invention, the oligosaccharides hereof preferably have about 5 to about 10 saccharide units per molecule. This range corresponds to unsubstituted saccharides having molecular weights ranging from about 650 to about 1300. Oligosaccharides having from about 5 to about 10 saccharide units per molecule are sometimes referred to herein as "simple" or "low molecular weight" oligosaccharides. Oligosaccharides are usually obtained by procedures of degradation of starches or cellulose which result in oligosaccharide fragments in a broad range of sizes.

A somewhat related family of materials are the glycosaminoglycans. They are structures comprising a polysaccharide skeleton, modified by a variety of substituents containing nitrogen, sulfur and oxygen atoms, and comprising various segments such as glucosamines, iduronates, glucuronates and the like. Their structures are variable between different samples of the same name group, such as the chondroitans, dermatans, hyaluronic acid, heparan sulfates, and heparins. Each family is known to be heterogenous, i.e., mixtures of compositions. Their molecular weight ranges generally between 10,000 and 25,000.

Substituted oligosaccharides, and, in particular, simple and low molecular weight oligosaccharides with polar or charged substituents, possess the ability to protect the kidneys from the nephrotoxic effect of certain classes of drugs. Anionically substituted cyclodextrins are preferred, at least in part, because of the relative uniformity, improved solubility in aqueous solution such as the bloodstream, decreased toxicity, improved clearance from the body and ease of production of such compounds, though other polar substituents such as OH may be used.

Anionic substituents include, by way of example, those described in U.S. Pat. No. 3,426,011. Oligosaccharides may be of the general formula:

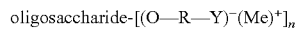

oligosaccharide-[(O—R—Y)⁻(Me)⁺]$_n$ where R is selected from the group consisting of straight chained or branched $C_{1-10}$ alkyl, alkenyl or alkynyl; $C_{3-8}$ cycloalkyl and $C_{3-8}$ aryl, each ring optionally containing 1 or more heteroatoms selected from S, N and O; and each of the aforementioned groups is optionally substituted with halo (i.e., F, Cl, Br, I) or hydroxyl;

Y is an acid group such as OH, COOH, $SO_3$, $SO_4$, $PO_3H$ or $PO_4$, or a phosphorous, phosphinous, phosphonic, phosphinic, thiophosphonic, thiophosphinic and sulfonic acid; or is absent;

Me is a pharmaceutically acceptable anion or cation, such as lithium, sodium, potassium, calcium, magnesium, or aluminum, or an organic primary, secondary, or tertiary amine such as methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like; and n is the number of substituents per oligosaccharide, each of which is independently selected, i.e., each substituent may be the same or different. "N" will be a whole number greater than 1, the upper limit dependent upon the particular oligosaccharide. In a population of oligosaccharides, it will be understood that n will represent the average number of substituents per molecule.

According to one embodiment, R is $C_{1-10}$ alkyl, preferably $C_{1-4}$ alkyl selected from methyl, ethyl, propyl and butyl, each optionally substituted with halo or hydroxyl. Specifically preferred are oligosaccharides where in one or more groups, Y is $SO_3$. The resulting preferred, polyanionically substituted oligosaccharides have molecular weights of from about 1600 to about 4000.

Cyclodextrins

In a preferred embodiment, the oligosaccharides are cyclic polysaccharides, preferably cyclodextrins, and more preferably derivatized cyclodextrins.

Cyclodextrins (also referred to as "CD" or "CDs") are cyclic oligosaccharides consisting of at least six glucopyranose units. Although CDs with up to twelve glucopyranose units are known, only the first three homologs have been studied extensively, α, β, and γ, having 6, 7 and 8 glucopyranose units, respectively. For example, the β-cyclodextrin molecule is made up of seven α-1,4-linked glucopyranose units which form a cone-shaped molecule having a hydrophilic outer surface and a lipophilic cavity in the center. It is believed that cyclodextrins exist as conical shaped molecules with the primary hydroxyls situated at the small end of the cone and the secondary hydroxyls situated at the large opening to the cone.

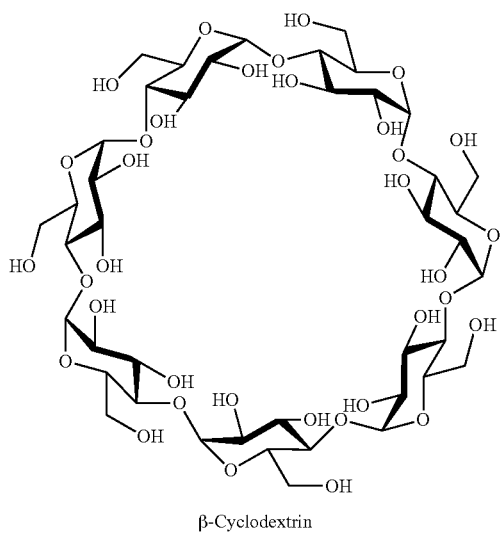 [SMILES: OCC1O[C@@H]2O[C@@H]3C(CO)O[C@H](O[C@@H]4C(CO)O[C@H](O[C@@H]5C(CO)O[C@H](O[C@@H]6C(CO)O[C@H](O[C@@H]7C(CO)O[C@H](O[C@@H]8C(CO)O[C@H](O[C@H]1[C@H](O)C2O)C(O)[C@H]8O)C(O)[C@H]7O)C(O)[C@H]6O)C(O)[C@H]5O)C(O)[C@H]4O)C(O)[C@H]3O]

β-Cyclodextrin

Topographically, the CDs may be represented as a torus, the upper rim of which is lined with primary —$CH_2OH$ groups, and the lower rim with secondary hydroxyl groups. Coaxially aligned with the torus is a channel-like cavity of about 5, 6 or 7.5 A.U. diameter for the α, β, and γ-CDs, respectively. These cavities make the cyclodextrins capable of forming inclusion compounds with hydrophobic guest molecules of suitable diameters.

A reasonably large number of CD derivatives have been prepared and described in the literature. In general, these chemically modified CDs are formed by reaction of the primary or secondary hydroxyl groups attached to carbons 2, 3 or 6, without disturbing the α (1→4) hemiacetal linkages. A review of such preparations is given in Croft et al., (*Tetrahedron* (1983) 39(9):1417-1474), incorporated herein by reference. Substitution via the hydroxyl groups on the glucopyranose units would include up to 18 for α-CD; 21 for β-CD; and 24 for γ-CD. The cyclodextrins may be selected from dextrins of the formula:

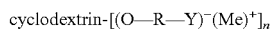

cyclodextrin-[(O—R—Y)$^-$(Me)$^+$]$_n$ where R, Y, Me and n are as described above. As will be apparent, n is 1 to 18 for α-CD; 1 to 21 for β-CD; and 1 to 24 for γ-CD.

Preferably, the cyclodextrin will have one or more substituents selected from the group consisting of hydroxyl, sulfonate, sulfate, carboxylate, phosphonate and phosphate. According to one embodiment, R is straight chained or branched $C_{1-10}$ alkyl, preferably $C_{1-4}$ alkyl selected from methyl, ethyl, propyl and butyl, each optionally substituted with halo or hydroxyl. Specifically preferred are oligosaccharides where in one or more groups, Y is $SO_3$.

Preferred CDs are sulfate or sulfonate derivatives of α, β, and γ-cyclodextrins. Preparation of cycloamylose sulfates and sulfonates, and modified cyclodextrin sulfates and sulfonates are described in the art. See, for example, U.S. Pat. Nos. 2,923,704; 4,020,160; 4,247,535; 4,258,180; 4,596,795 and 4,727,064, each of which is hereby incorporated by reference. These cyclodextrin sulfates and sulfonates are typically associated with a physiologically acceptable cation.

According to another embodiment, the hydroxyl groups are substituted with alkyl ether sulfonates of the formula —O—($C_1$-$C_8$ alkyl)-$SO_3$. In one example, commercially available Captisol® (Cyclex) may be used which is a sulfobutyl ether derivative of β-cyclodextrin having an average of seven sulfobutyl ether groups per cyclodextrin molecule (i.e., O—R—Y is —O—$(CH_2)_4$—$SO_3^-Na^+$) (alternatively referred to herein as sulfobutyl ethyl β cyclodextrin or SBE-βCD). Captisol does not exhibit the nephrotoxicity associated with underivitized β-cyclodextrin. Additional cyclodextrin derivatives are disclosed in U.S. Pat. Nos. 5,134,127; 6,165, 995; 6,479,467 (e.g., hydroxybutenyl-cyclodextrins); and 6,060,597, and patent publication 20060258537 (SAE-AE-CD), each of which is hereby incorporated by reference. Additional CDs include methylated derivatives with, for example, an average MS of 14 (M14-b-CD), and glucosyl and maltosyl CDs containing mono-(G1-b-CD) and disaccharide (G2-b-CD) substituents. Additional cyclodextrins are set forth below (adapted from Mosher et al., Encyclopedia of Pharm. Tech. (2002) 531-58).

| | Nomenclature and substituent structures for modified CDs | | |
|---|---|---|---|
| | Position of substituent | Substituent structure$^a$ | Nomenclature #$^b$-XYZ$^c$#$^d$-CD$^e$ |
| Parent cyclodextrins | | | |
| Alpha-CD | | —OH | α-CD |
| Beta-CD | | —OH | β-CD |
| Gamma-CD | | —OH | γ-CD |
| Modified cyclodextrins neutral | | | |
| Methyl derivatives | | | |
| Dimethyl | 2,6- | —O—$CH_3$ | 2,6-DM14-CD |
| Methyl | Random | —O—$CH_3$ | M#-CD |
| Trimethyl | 2,3,6- | —O—$CH_3$ | 2,3,6-TM-CD |
| Ethyl derivatives | Random | —O—$CH_2$—$CH_3$ | E#-CD |
| Hydroxyalkyl derivatives | | | |
| 2-hydroxyethyl | Random | —O—$CH_2$—$CH_2OH$ | (2HE)#-CD |
| 2-hydroxypropyl | Random | —O—$CH_2$—CHOH—$CH_3$ | (2HP)#-CD or HP#-CD |
| 3-hydroxypropyl | Random | —O—$CH_2$—$CH_2$—$CH_2OH$ | (3HP)#-CD |
| 2,3-dihydroxypropyl | Random | —O—$CH_2$—CHOH—$CH_2OH$ | (2,3-DHP)#-CD |
| Modified cyclodextrins anionic | | | |
| Carbon Based Derivatives | | | |
| Carboxy | 6- | —$CO_2M$ | 6-C#-CD |
| Carboxyalkyl | | | |
| Carboxymethyl | Random | —O—$CH_2$—$CO_2M$ | CM#-CD |
| Carboxyethyl | Random | —O—$CH_2$—$CH_2$—$CO_2M$ | CE#-CD |
| Carboxypropyl | Random | —O—$CH_2$—$CH_2$—$CH_2$—$CO_2M$ | CP#-CD |
| Carboxylmethyl ethyl | 2,6-; 3- | —O—$CH_2$—$CO_2M$; —O—$CH_2$—$CH_3$ | CME#-CD |
| Sulfur Based Derivatives | | | |
| Sulfates | 2,6-random | —O—$SO_3M$ | S#-CD |
| Alkylsulfates | 6- | —O—$(CH_2)_{11}$—O—$SO_3M$ | SU#-CD |
| Sulfonates | 6- | —$SO_3M$ | 6-SA#-CD |

-continued

Nomenclature and substituent structures for modified CDs

| | Position of substituent | Substituent structure[a] | Nomenclature #[b]-XYZ[c]#[d]-CD[e] |
|---|---|---|---|
| Alkylsulfonates | | | |
| Sulfoethyl ether | Random | —O—$(CH_2)_2$—$SO_3M$ | SEE#-CD |
| Sulfopropyl ether | Random | —O—$(CH_2)_3$—$SO_3M$ | SPE#-CD |
| Sulfobutyl ether | Random | —O—$(CH_2)_4$—$SO_3M$ | SBE#-CD |

[a]M: Cation
[b]Numbers represent position of substituents if known; if the preparation is a random distribution, then no notation implies an undefined distribution at the 2-, 3-, and 6-positions.
[c]Letters represent abbreviated notation of substituent.
[d]Numbers represent the average MS rounded to the closest whole number.
[e]Indication of parent CD structure, i.e., α-CD.

In another preferred embodiment, the cyclodextrin is of the formula:

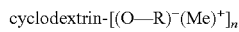

where R is selected from the group consisting of straight-chained or branched $C_{1-10}$ alkyl, alkenyl or alkynyl; substituted with 1 or more hydroxyl. In one embodiment, O—R is O—$CH_2CH(OH)CH_3$, i.e, the cylcodextrin is 2-hydroxypropyl β-cyclodextrin (HPβCD). In one embodiment, the degree of substitution is 4.7, as used in the Examples below.

The nephrotoxic drug may be any pharmaceutical agent including small molecules and peptides that cause renal damage upon administration to a host. Such drugs include, by way of example, diuretics, NSAIDs, ACE inhibitors, cyclosporin, tacrolimus, radiocontrast media, interleukin-2, vasodilators (hydralazine, calcium-channel blockers, minoxidil, diazoxide), mitomycin C, conjugated estrogens, quinine, 5-fluorouracil, ticlopidine, clopidogrel, interferon, valacyclovir, gemcitabine, bleomycin, heparin, warfarin, streptokinase, aminoglycosides, cisplatin, nedaplatin, methoxyflurane, tetracycline, amphotericin B, cephaloridine, streptozocin, tacrolimus, carbamazepine, mithramycin, quinolones, foscarnet, pentamidine, intravenous gammaglobulin, fosfamide, zoledronate, cidofovir, adefovir, tenofovir, mannitol, dextran, hydroxyethylstarch, lovastatin, ethanol, codeine, barbiturates, diazepam, quinine, quinidine, sulfonamides, hydralazine, triamterene, nitrofurantoin, mephenylion, penicillin, methicillin ampicillin, rifampin, sulfonamides, thiazides, cimetidine, phenyloin, allopurinol, cephalosporins, cytosine arabinoside, furosemide, interferon, ciprofloxacin, clarithromycin, telithromycin, rofecoxib, pantoprazole, omeprazole, atazanavir, gold, penicillamine, captopril, lithium, mefenamate, fenoprofen, mercury, interferon, pamidronate, fenclofenac, tolmetin, foscarnet, aciclovir, methotrexate, sulfanilamide, triamterene, indinavir, foscarnet, ganciclovir, methysergide, ergotamine, dihydroergotamine, methyldopa, pindolol, hydralazine, atenolol, taxol, tumor necrosis factor, chlorambucil, interleukins, bleomycin, etoposide, fluorouracil, vinblastine, doxorubicin, cisplatin and the like (see, generally, Devasmita et al., *Nature Clinical Practice Nephrology* (2006) 2, 80-91).

Methotrexate

According to one embodiment, the nephrotoxic drug is methotrexate, or a derivative or pharmaceutically acceptable salt thereof. Methotrexate (N-[4-[[(2,4-diamino-6pteridinyl)methyl]methylamino]benzoyl]-L-glutamicacid) is an S-phase chemotherapeutic antimetabolite used for the treatment of various neoplasms, particularly CNS lymphoma. MTX is one the most widely used anticancer agents and is employed in the treatment of neoplastic diseases such as gestational choriocarcinoma, osteosarcoma, chorioadenoma destruens, hydatidiform mole, acute lymphocytic leukemia, breast cancer, epidermoid cancers of the head and neck, advanced mycosis fungoides, lung cancer, and non-Hodgkins lymphomas (Physicians Desk Reference (45th ed.), Medical Economical Co., Inc., 1185-89 (Des Moines, Iowa (1991))). MTX is also an effective immunosuppressive agent, with utility in the prevention of the graft-versus-host reaction that can result from tissue transplants, as well as in the management of inflammatory diseases. Consequently, MTX can be employed in the treatment of severe and disabling psoriasis and rheumatoid arthritis (Hoffmeister, *The American Journal of Medicine* (1983) 30:69-73; Jaffe, *Arthritis and Rheumatism* (1988) 31: 299).

However, methotrexate is associated with renal and hepatic toxicity when applied in the "high dose regimen" that is typically required for maximum efficiency (Barak et al., *J. American Coll. Nutr.* (1984) 3:93-96).

Numerous patents disclose MTX and MTX analogs, any of which may be used in practicing the present invention. See, for example, U.S. Pat. Nos. 2,512,572, 3,892,801, 3,989,703, 4,057,548, 4,067,867, 4,079,056, 4,080,325, 4,136,101, 4,224,446, 4,306,064, 4,374,987, 4,421,913, 4,767,859, 3,981,983, 4,043,759, 4,093,607, 4,279,992, 4,376,767, 4,401,592, 4,489,065, 4,622,218, 4,625,014, 4,638,045, 4,671,958, 4,699,784, 4,785,080, 4,816,395, 4,886,780, 4,918,165, 4,925,662, 4,939,240, 4,983,586, 4,997,913, 5,024,998, 5,028,697, 5,030,719, 5,057,313, 5,059,413, 5,082,928, 5,106,950, 5,108,987, 4,106,488, 4,558,690, 4,662,359, 6,559,149, each of which is hereby incorporated by reference. Other MTX analogs and related antifolate compounds include trimetrexate, edatrexate, AG331, piritrexim, 1843U89, LY 231514, ZD 9331, raltritrexed, lometrexol, MTA and AG337 (Takimoto, *Seminars in Oncology* (1997) 24:S18-40-51; Sorbello et al., *Haematoligica* (2001) 86:121-27); CB 3717, LY 309887 (Calvert, *Seminars in Oncology* (1999) 26:S6, 3-10; Rosowsky, *Progress in Med. Chem.* (1989) 26:1-237)).

Accordingly, the compositions disclosed herein may be used for treating cancer or for inhibiting the growth of cancer; as well as for treating multiple sclerosis, and the symptoms associated therewith. The compositions may be used in conjunction with or in combination with other active agents such as interferon. Additionally, the compositions may be used for treating autoimmune disorders such as lupus and rheumatoid arthritis.

Antibiotics

Aminoglycoside antibiotics, such as gentamicins, kanamycins, streptomycins and tobramycins, are generally utilized as broad spectrum antimicrobials effective against, for example, gram-positive, gram-negative and acid-fast bacteria. However, aminoglycosides are often associated with undesired side-effects such as nephrotoxicity and ototoxicity. Other antibiotics which may used in the practice of the present invention include acylovir, vancomicin and cephalosporin, such as Rocephin® and Kefzol.

Non-Steroidal Anti-Inflammatory Drugs (NSAIDs)

NSAIDs all present renal toxicity. NSAIDs typically are used to reduce pain while avoiding the use of opiate derivatives. Two widely used NSAIDs are Indomethacin and Toradol® manufactured by Roche Pharmaceuticals.

Antifungal Agents

Caspofungin and amphotericin B are both known to be nephrotoxic, and may be used in practicing the disclosed invention.

Anti-Cancer Agents

Many anti-cancer agents exhibit dose limiting renal toxicity and may be used in practicing the present invention. Such agents include, by way of example, cisplatin, doxyrubicin, cyclophosphamide, butasulfane, and the like.

Contrast Agents

Contrast agents are injected into a patient prior to x-ray scans. Contrast agents are highly concentrated (50-66% solutions) iodinated compounds. In view of this high concentration it is likely that only a minimum of a 1:1 ratio of contrast agent to cyclodextrin would be necessary, and up to about 10 to 1 or higher. Examples of the possible use of cyclodextrin to protect against renal damage by contrast agents include Iohexyl and Ioversol. Other contrast agents that may be used in practicing the present invention include diatrizoate meglumine and ioxaglate.

Administration

The oligosaccharide may be complexed with the nephrotoxic drug, although it is not believed necessary for antinephrotoxic protective effect of the composition. The ratio of drug to oligosaccharide is preferably within a range such that the drug does not precipitate at pH typically found in the kidney, taking into account the transit time of the drug through the kidney. In some cases, it may be desirable to minimize the amount of oligosaccharide in vivo. Simple in vitro solubility experiments such as described in the Examples may be used to determine the minimum amount of oligosaccharide needed to effectively protect from renal damage. Alternatively, the minimum amount of oligosaccharide needed to effectively protect the kidney from damage can be determined in animal studies of the effect of the oligosaccharide on drug induced kidney pathology.

In one embodiment, the molar ratio of drug:oligosaccharide is greater than 1:1, and may range from about 1.1:1 to about 50:1, preferably from about 1.25:1 to about 25:1; more preferably from about 1.75:1 to about 2:1 to about 10:1. In the case of methotrexate, by way of example only, it was found that a mole ratio of about 2:1 methotrexate:Captisol worked well to keep methotrexate in solution in vitro and provided the desired nephrotoxic effect. Where lower amounts of oligosaccharides are desired, it is contemplated that additional solubilizing agents may be used, provided that the amount of oligosaccharide in the composition remains sufficient to provide a renal protective effect. By way of example, in the case of the contrast agent iohexyl, as shown in the Examples, a mole ratio of about 10:1 iohexyl to SBEβCD worked well to markedly reduce the kidney pathology in iohexyl induced kidney damage in mice.

It may be desirable in some cases to have a ratio of drug to oligosaccharide lower than 1:1 where, for example, the binding constant of the drug is low or where the drug is processed by the kidneys at a lower rate than the cyclodextrin, it may be beneficial to have a molar excess of oligosaccharide. This may be true for many classes of drugs where the dose of the drug required for a therapeutic effect is low, therefore, although the molar ratio of oligosaccharide might be higher, the absolute amount or concentration in vivo is not necessarily increased. As such, the composition may comprise from about 2 to about 50; from about 2 to about 20; or from about 2 to about 10 times molar excess of the oligosaccharide, or preferably in the range of from about 1 to about 5:1, and more preferably in the range of about 2 to about 5:1, oligosaccharide to drug.

Further provided are methods of reducing the nephrotoxic effect of a pharmaceutically active compound comprising contacting the compound with a polyanionic oligosaccharide. Methods are included for inhibiting or reducing nephrotoxicity associated with a nephrotoxic drug, comprising administering a pharmaceutical composition comprising a polyanionic oligosaccharide, the nephrotoxic drug and optionally a pharmaceutically acceptable carrier. Although it is preferred that administration occur as a single dose, particularly where the oligosaccharide assists in solubolizing the drug, the methods may also be effected by concurrently administering a pharmaceutical composition comprising a polyanionic oligosaccharide and a pharmaceutical composition comprising the nephrotoxic inducing drug, i.e., in separate doses. Where the drug and oligosaccharide are combined into a single dosage unit, they may be combined with a pharmaceutically acceptable carrier, for example, a cosolution or dispersion in an inert pharmaceutically acceptable solvent or dispersing agent or the like.

Alternatively, the oligosaccharide can be separately formulated with pharmaceutically acceptable materials and administered separately; either concurrently with the drug or within about an hour before or after administration of the drug. By concurrently, it is meant administration of the separate doses occurs substantially at the same time such that both the oligosaccharide and the drug are present in vivo. Alternatively, administration may occur sequentially provided that the oligosaccharides are present within the renal environment as the concentration of drug in the kidney increases to levels at which the toxic effect of the drug may occur.

The mode of administration, the dosage and frequency of dosage is governed by the mode of administration and dosage considerations conventionally employed with the pharmaceutical agent. Thus, for example, various combinations of the invention can be administered intramuscularly or intravenously, or otherwise, as dictated by medical and pharmacological practice related to the desired use of the particular drug or agent employed. Administration may be achieved orally or parenterally including, inter alia, topical application, intravenous, intra-arterial or subcutaneous injection, and including absorption as well as injection and introduction into body apertures or orifices.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The other features of the invention will become apparent in the course of the following descriptions of exemplary embodiments which are given for illustration of the invention and are not intended to be limiting thereof.

EXAMPLES

Example 1

Effect of pH on Solubility of MTX

Solubility studies were performed to determine whether Captisol could prevent the precipitation of MTX over a time period greater than transit time of MTX through the kidney (i.e., less than 2 minutes). Solutions were prepared as shown in the Table 1. Each solution was acidified with HCl, centrifuged and aliquots of the supernatant removed as a function of time, and the concentration of MTX in solution was measured spectrophometrically.

As shown in FIG. 1, Captisol prevented the precipitation of MTX at a concentration dependent rate. At a mole ratio of 1:1, the MTX remains in solution indefinitely. At lower ratios, precipitation occurs at a concentration dependent rate. At 0.50:1 ratio of Captisol to MTX, MTX remains in solution for at least 15 minutes, and at a ratio of 0.25:1, much of it remains for 10 minutes. In view of the rapid transit time of filtration in the kidneys, in vivo experiments to determine the optimal ratio of MTX to Captisol to prevent kidney damage may be performed.

TABLE 1

MTX-captisol solubility
MTX added: 0.91 mg/ml
Concentration of MTX: 0.002M
Rate of precipitation of MTX at pH 5.0 in presence and absence of captisol
Captisol:MTX molar ratio 1:1

| Captisol added (mM) | Time after adding acid (min) | OD at 302-304 nm | Amount of MTX in solution (ug/mL) | correction for dilution 1:25 dilution ug/ml | | conc. of MTX (M) | captisol/MTX ratio |
|---|---|---|---|---|---|---|---|
| | | | | | mg/ml | | |
| 0.002 | 5 | 2.71 | 33.28800989 | 832.2002 | 0.8322 | 0.0018308 | 1:1 |
| 0.002 | 10 | 2.291 | 28.10877627 | 702.7194 | 0.702719 | 0.001546 | 1:1 |
| 0.002 | 15 | 2.296 | 28.17058096 | 704.2645 | 0.704265 | 0.0015494 | 1:1 |
| 0.002 | 20 | 2.127 | 26.0815822 | 652.0396 | 0.65204 | 0.0014345 | 1:1 |
| 0.002 | 30 | 2.067 | 25.33992583 | 633.4981 | 0.633498 | 0.0013937 | 1:1 |
| 0.002 | 40 | 2.202 | 27.00865266 | 675.2163 | 0.675216 | 0.0014855 | 1:1 |
| 0.002 | 50 | 2.078 | 25.47589617 | 636.8974 | 0.636897 | 0.0014012 | 1:1 |
| 0.002 | 60 | 2.004 | 24.56118665 | 614.0297 | 0.61403 | 0.0013509 | 1:1 |

Captisol:MTX molar ratio 0.5:1

| Captisol added (M) | Time after adding acid (min) | OD at 302-304 nm | MTX in solution (ug/mL) | correction for dilution 1:500 1:25 dilution ug/ml | | conc. of mtx (M) | captisol/MTX ratio |
|---|---|---|---|---|---|---|---|
| | | | | | mg/ml | | |
| 0.001 | 5 | 1.854 | 22.70704574 | 567.6761 | 0.567676 | 0.0012489 | 0.5:1 |
| 0.001 | 10 | 2.263 | 27.76266996 | 694.0667 | 0.694067 | 0.0015269 | 0.5:1 |
| 0.001 | 15 | 2.594 | 31.85414091 | 796.3535 | 0.796354 | 0.001752 | 0.5:1 |
| 0.001 | 20 | 1.531 | 18.7144623 | 467.8616 | 0.467862 | 0.0010293 | 0.5:1 |
| 0.001 | 30 | 1.044 | 12.6946848 | 317.3671 | 0.317367 | 0.0006982 | 0.5:1 |
| 0.001 | 40 | 0.959 | 11.64400494 | 291.1001 | 0.2911 | 0.0006404 | 0.5:1 |
| 0.001 | 50 | 0.864 | 10.4697157 | 261.7429 | 0.261743 | 0.0005758 | 0.5:1 |
| 0.001 | 60 | 0.861 | 10.43263288 | 260.8158 | 0.260816 | 0.0005738 | 0.5:1 |

Captisol:MTX molar ratio 0.25:1

| Captisol added (M) | Time of OD min after adding acid | OD at 302-304 nm | conc of MTX (ug/mL) | dilution 1:500 ug/ml | mg/ml | molarity of mtx (M) | captisol/MTX ratio |
|---|---|---|---|---|---|---|---|
| 0.0005 | 5 | 2.363 | 28.99876391 | 724.9691 | 0.724969 | 0.0015949 | 0.25:1 |
| 0.0005 | 10 | 1.798 | 22.01483313 | 550.3708 | 0.550371 | 0.0012108 | 0.25:1 |
| 0.0005 | 15 | 1.173 | 14.28924598 | 357.2311 | 0.357231 | 0.0007859 | 0.25:1 |
| 0.0005 | 20 | 0.864 | 10.4697157 | 261.7429 | 0.261743 | 0.0005758 | 0.25:1 |
| 0.0005 | 30 | 0.686 | 8.26946848 | 206.7367 | 0.206737 | 0.0004548 | 0.25:1 |
| 0.0005 | 40 | 0.633 | 7.61433869 | 190.3585 | 0.190358 | 0.0004188 | 0.25:1 |
| 0.0005 | 50 | 0.556 | 6.662546354 | 166.5637 | 0.166564 | 0.0003664 | 0.25:1 |
| 0.0005 | 60 | 0.556 | 6.662546354 | 166.5637 | 0.166564 | 0.0003664 | 0.25:1 |

Captisol:MTX molar ratio 0:1

| Captisol added (M) | Time of OD min after adding acid | OD at 302-304 nm | conc of MTX (ug/mL) | dilution 1:500 ug/ml | mg/ml | molarity of mtx (M) | captisol/MTX ratio |
|---|---|---|---|---|---|---|---|
| 0 | 5 | 0.296 | 3.448702101 | 86.21755 | 0.086218 | 0.0001897 | 0:1 |
| 0 | 10 | 0.22 | 2.509270705 | 62.73177 | 0.062732 | 0.000138 | 0:1 |
| 0 | 15 | 0.274 | 3.176761434 | 79.41904 | 0.079419 | 0.0001747 | 0:1 |
| 0 | 20 | 0.328 | 3.844252163 | 96.1063 | 0.096106 | 0.0002114 | 0:1 |

TABLE 1-continued

MTX-captisol solubility
MTX added: 0.91 mg/ml
Concentration of MTX: 0.002M
Rate of precipitation of MTX at pH 5.0 in presence and absence of captisol
Captisol:MTX molar ratio 1:1

| 0 | 30 | 0.325 | 3.807169345 | 95.17923 | 0.095179 | 0.0002094 | 0:1 |
|---|----|-------|-------------|----------|----------|-----------|-----|
| 0 | 40 | 0.284 | 3.300370828 | 82.50927 | 0.082509 | 0.0001815 | 0:1 |
| 0 | 50 | 0.293 | 3.411619283 | 85.29048 | 0.08529  | 0.0001876 | 0:1 |
| 0 | 60 | 0.333 | 3.90605686  | 97.65142 | 0.097651 | 0.0002148 | 0:1 |

Example 2

Protective Effect of Captisol-MTX

A comparison of the effect of MTX 40 mg/kg with and without Captisol® (molar ratio 1:1) in myelin-oligodendrocyte-glycoprotein (MOG) induced experimental autoimmune encephalomyelitis (EAE) in C57BL6 mice was performed. Clinical signs, CNS pathology and renal pathology were measured.

EAE was induced as follows. Mice were anesthetized with Avertin (222 tribromoethanol) and given two subcutaneous injections of 150 µg of MOG in PBS (total dose 300 µg) that had been emulsified in an equal volume of Freund's incomplete adjuvant containing 250 µg of *M. tuberculosis* $H_{37}RA$ (total dose 500 µg). One injection was given at the nape and the second was given on the dorsum. Pertussis toxin (100 ng; i.v. through the tail vein) was administered on days 0, 3, and 7 following encephalitogen.

Stock MTX was used at 25 mg/ml (Bedford laboratories). MTX stock was diluted 3.67 times with PBS (2 ml stock+5.34 ml PBS) for a total volume of 7.34 ml, at a concentration of 6.8 mg/ml (14.9 mM).

3.00 ml of diluted MTX solution was aliquoted and added to 96.6 mg of Captisol powder, and the solution vortex mixed. The resulting solution was mostly clear but pale yellow. All solutions were kept at RT in dark until ready to inject. 96.6 mg/3 ml=32.228 mg/ml=14.9 mM; MTX:Captisol molar ratio 1:1.

The test mixtures were administered to 5 groups of mice (Groups I-V; see Table 2).

TABLE 2

| Groups    | EAE/control | Treatment                            | Number of mice |
|-----------|-------------|--------------------------------------|----------------|
| Group I   | EAE         | PBS                                  | 5              |
| Group II  | EAE         | MTX 40 mg/kg                         | 10             |
| Group III | EAE         | MTX 40 mg/kg + captisol (molar ratio 1:1) | 10        |
| Group IV  | EAE         | Captisol only 201.25 mg/kg           | 10             |
| Group V   | EAE         | No treatment                         | 5              |

Twenty four (24) hours after symptom onset, MTX (40 mg/kg body weight) was administered via tail vein. Injection volume were between 100-120 µl. MTX+Captisol was injected in a volume of 100-120 µl via tail vein. Captisol alone (32.22 mg/ml) was injected via tail vein in a volume of 100-120 µl Leukovorin (20 mg/kg body weight) was injected via tail vein 4 hours after MTX injection and again 24 hours after. Leukovorin, the active metabolite of folic acid, is typically given with methotrexate in anti-cancer chemotherapy to help protect normal cells.

Animals were weighed and scored daily for clinical signs. Scores were based on the following on the following signs:
0—normal
1—flacid tail, piloerection, and/or weight loss
2—hind limb weakness righting difficulty
3—hind limb weakness causing righting inability
4—hindlimb paresis, limp walking, and or/incontinence
5—partial hind limb paralysis
6—total hind limb paralysis plus forelimb weakness
7—total hind limb paralysis plus forelimb paresis or paralysis
8—death or moribund requiring sacrifice Mice were scored daily for disease severity and then sacrificed on day 10 of disease. Brain, kidney and spleen were formalin fixed. To assess the infiltration of T cells into the CNS, CD3+ immunohistochemistry was performed on paraffin embedded 8 micron thick hind brain sections of untreated EAE mice and EAE mice treated concurrently with MTX and captisol. For light microscopic investigation, kidneys were fixed in 10% buffered formalin and processed routinely for paraffin embedding. Tissue sections of 5 micron meter were stained with hematoxylin and eosine and examined under Nikon coolpix light microscope.

The severity of total kidney damage was evaluated by a semiquantitative measurement of damage as described. Each tissue section of the kidney was assessed for degeneration of glomerular structure, glomerular crowding and congestion, dilation of bowman space, degeneration of proximal and distal tubules, and dilation of renal tubules, vascular congestion, and inflammatory cell infiltration. For glomerular atrophy, glomeruli that contained more than 20 nuclei were scored "0", and those containing less than 10 nuclei were scored "4." Intermediate stages were 1, 2 and 3. Other criterion was scored on a 0-3 scale: 0=none; 1=mild; 2=moderate; 3=severe.

Figure 2:
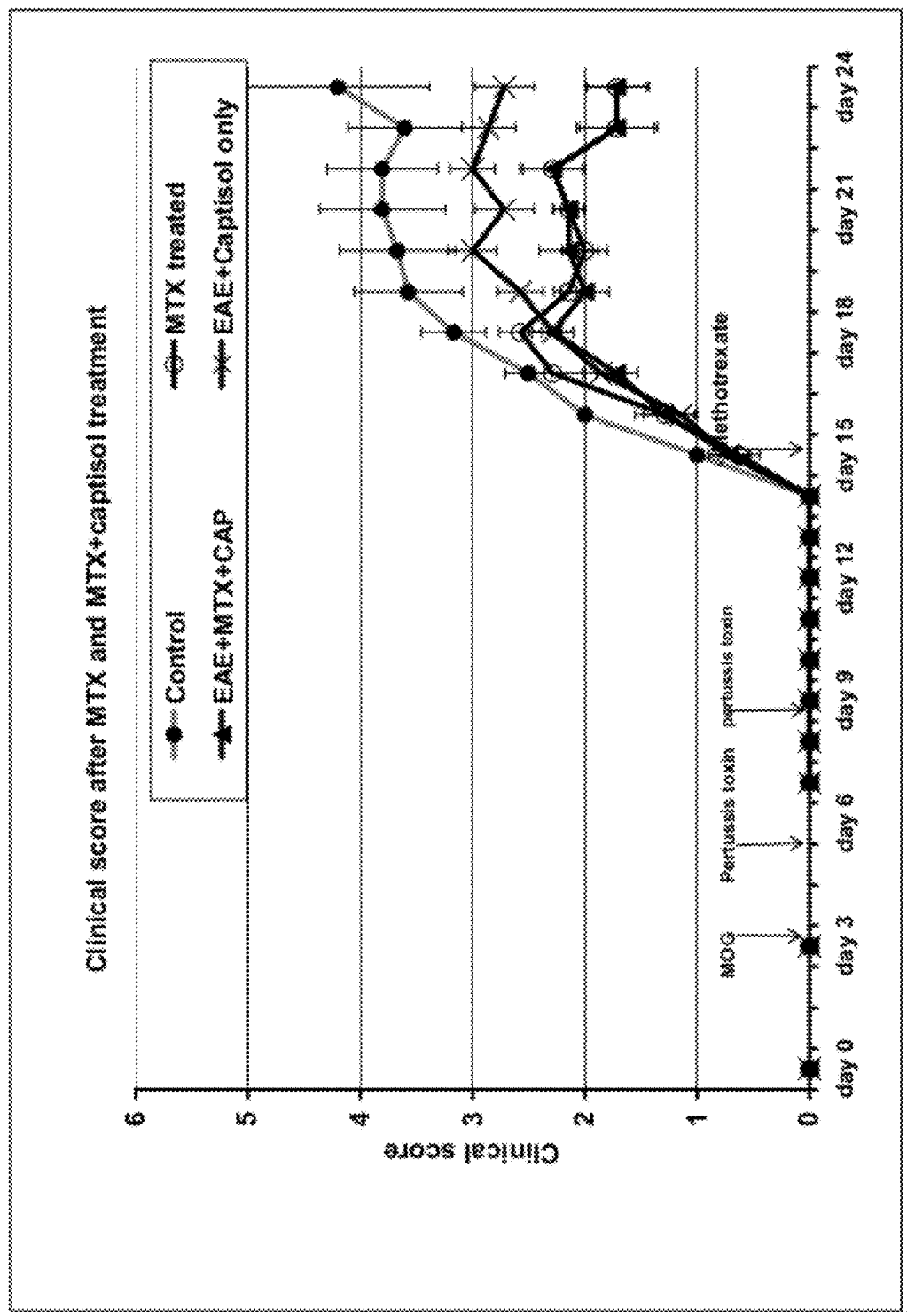
FIG. 2 shows renal pathology scores indicative of total kidney damage in myelin-oligodendrocyte-glycoprotein (MOG) induced experimental autoimmune encephalomyelitis (EAE) mouse model following treatment with MTX and MTX+captisol.

The microscopic score of each tissue was calculated as the sum of the scores given to each criterion and at least 100 nephrons (glomeruli plus surrounding tubules) were analyzed per section. Data is represented as mean±SEM (see FIG. 2).

MOG treated mice developed severe clinical manifestation, starting on days 10-11. They were maintained until sacrifice at 13 days. All animal were affected. Partial or complete hind leg paralysis (clinical score).

Efficacy of MTX 40 mg/kg+Captisol was comparable to the efficacy seen with MTX treatment alone.

The result of the CNS Pathology-CD3+ Immunostaining showed that untreated EAE mice had extensive infiltration of CD3+ T cells in the hind brain and spinal cord (not shown). EAE mice treated post-symptomatically with concurrently MTX+Captisol (40 mg/kg+captisol 1:1 molar ratio) showed 80-90% reduction in T cell infiltration (not shown). The efficacy of MTX+Captisol was comparable to the efficacy with MTX treatment alone.

Figure 3:
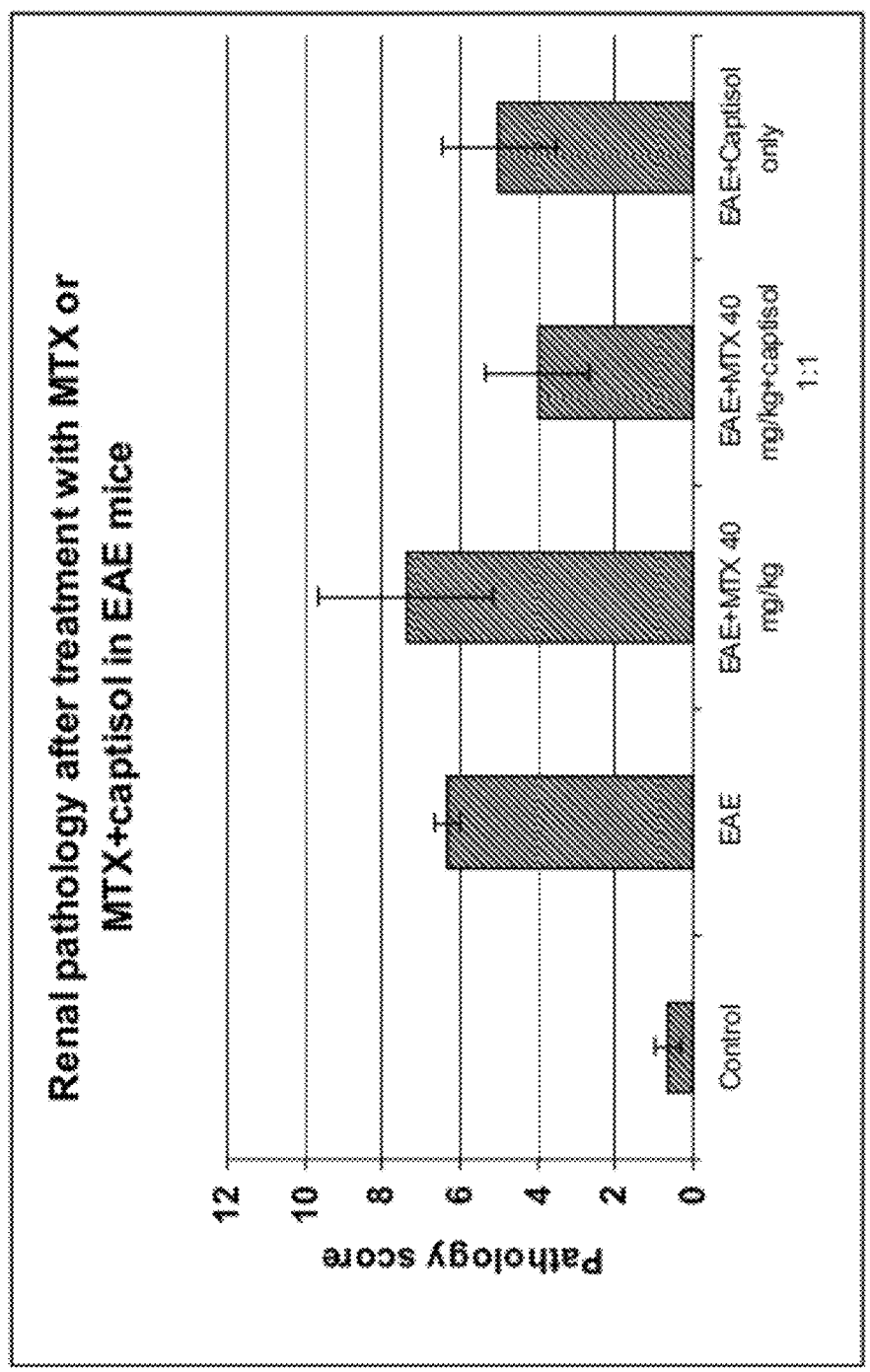
FIG. 3 shows clinical scores after treatment with MTX or MTX+captisol in EAE mice.

Renal pathology scores are shown in FIG. 3. Kidney sections from 3 different EAE mice treated with MTX 40 mg/kg, showed dilation of renal tubules and degeneration of proximal tubules. Kidney sections from mice treated concurrently with MTX+Captisol showed a protective effect on tubules. A single intravenous bolus injection of 40 mg/kg MTX produced morphological changes in the kidney which was mostly restricted to dilation of renal tubules in the cortex. Concurrent Captisol administration with MTX resulted in reduction in pathology score in the EAE mice.

MTX and Captisol were administered to 8 groups of mice (Groups I-VIII; see Table 3) via tail vein by a single injection in a volume of 100-120 μL. Animals were sacrificed after 48 hours. Clinical symptoms, body weights were recorded. Kidneys were preserved (one frozen, one formalin fixed) for pathology. Leukovorin was given at 4 hours and after 18 hours. Urine was not alkalinized.

TABLE 3

| GROUPS | | TREATMENT | Molarity of MTX | Molarity of Captisol | Molar ratio MTX:Captisol | # of mice |
|---|---|---|---|---|---|---|
| Group I | Normal mice | MTX only, 80 mg/kg, iv bolus. Solution A | 26.4 mM | | | 3 |
| Group II | Normal mice | MTX only, 120 mg/kg, iv, bolus. Solution B | 39.6 mM | | | 3 |
| Group III | Normal mice | MTX only, 160 mg/kg, iv, bolus. Solution C | 53 mM | | | 1 |
| Group IV | Normal mice | MTX, 80 mg/kg, iv + Captisol 382 mg/kg body weight. Solution D | 26.4 mM | 26.4 mM | 1:1 | 3 |
| Group V | Normal mice | MTX, 120 mg/kg, iv + Captisol 570 mg/kg. Solution E | 39.6 mM | 39.6 mM | 1:1 | 3 |
| Group VI | Normal mice | MTX, 160 mg/kg, iv + Captisol 764 mg/kg body weight. Solution F | 53 mM | 53 mM | 1:1 | 1 |
| Group VII | Normal mice | MTX, 80 mg/kg, iv + Captisol 191 mg/kg. Solution G | 26.4 mM | 13.2 mM | 1:0.5 | 3 |
| Group VIII | Normal mice | MTX, 120 mg/kg, iv + Captisol 285 mg/kg. Solution H | 39.6 mM | 19.8 mM | 1:0.5 | 3 |

Example 3

Captisol-MTX at Various Molar Ratios

A study of histopathological changes in the kidney after single bolus intravenous MTX with or without concurrent captisol at different molar ratios was performed.

MTX solutions were prepared as follows. Solution A (24 mg/ml (53 mM)) was prepared from stock solution of 25 mg/ml (Methotrexate from Bedford laboratories) in sterile PBS (total volume 6 mL). Solution B was prepared by diluting 3 ml of Solution A to 1:1.33 in PBS to obtain a working dilution of 18 mg/mL (39.6 mM), pH 7.4. Solution C was prepared by diluting 2 mL of solution A 1:2 to obtain a working dilution of 12 mg/mL (26.4 mM), pH 7.2.

MTX+Captisol solutions were prepared as follows. Solution D was made by adding 57.32 mg Captisol to an aliquot of 500 micro liter of solution A (molar ratio 1:1, neutral pH). Solution E was made by adding 85.6 mg Captisol to 1 mL aliquot of solution B (molar ratio 1:1, neutral pH). Solution F was made by adding 57.10 mg Captisol to 1 mL aliquot of solution C (molar ratio 1:1, neutral pH). Solution G was prepared by adding 42.8 mg Captisol to 1 mL aliquot of solution B. Solution H was made by adding 28.6 mg of Captisol to 1 mL aliquot of solution C.

Figure 4:
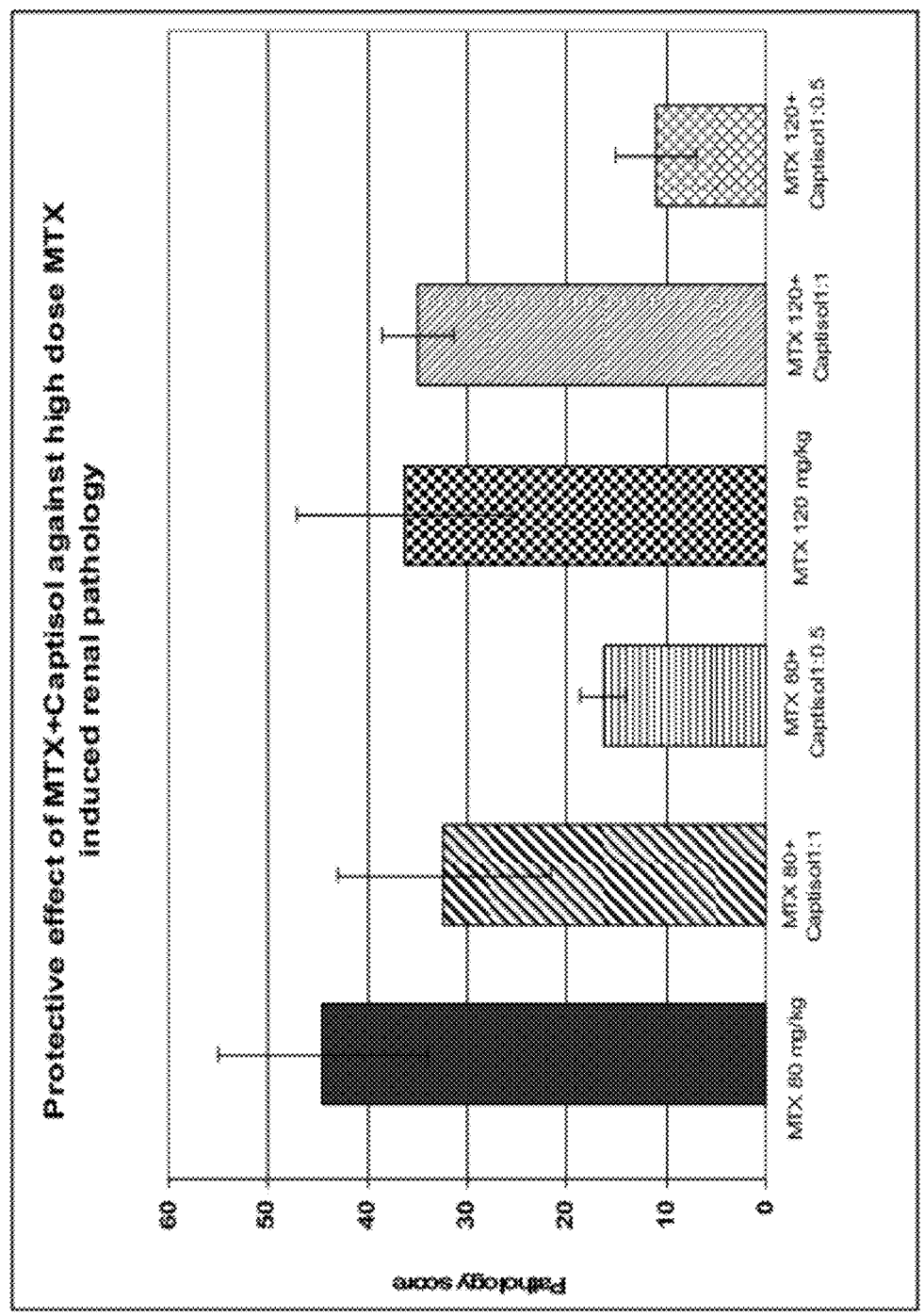
FIG. 4 shows renal pathology scores in kidney sections after single bolus intravenous MTX with or without concurrent captisol at different molar ratios in normal mice.

Semi quantitative estimates of total kidney damage in mice treated with MTX 80 mg/kg, 120 mg/kg, and a combination of MTX+Captisol at MTX to Captisol molar ratio of 1:1 and 1:0.5, are shown in FIG. 4. The scores for the control kidney were between 3-4 (not shown in the graph). Hematoxylin and eosin sections of paraffin embedded kidney were analyzed microscopically for extent of renal damage. Data is expressed as mean±SEM. Data for MTX 160 mg/kg is not included in the graph as there was only a single mouse in this group.

Paraffin sections of the kidneys stained with hematoxylin and eosin (not shown) showed that kidneys from mice administered 80 mg/kg MTX had dilation of tubules, degenerative changes in the tubules, hypercellularity in the glomerulus and atypical collection of interstitial cells and convulated tubules. Kidneys from mice administered 80 mg/kg MTX+Captisol at MTX to Captisol molar ratio 1:1, and 80 mg/kg MTX+Captisol at MTX to Captisol molar ratio 1:0.5, showed milder degeneration of tubules, normal glomerulus, and no infiltration of inflammatory cell. However, the degree of kidney protection was much higher when the molar ratio of MTX to Captisol was 1:0.5.

Paraffin sections of kidney stained with hematoxylin and eosin (not shown) showed that kidneys from mice administered 120 mg/kg MTX, IV had glomerular atrophy, degeneration of basement membrane on bowman capsule, degenerative changes in the tubules, hypercellularity in the glomerulus and infiltration of mononuclear cells. Kidneys from mice administered 120 mg/kg MTX+captisol at MTX to Captisol molar ratio of 1:1, and 120 mg/kg MTX+captisol at MTX to Captisol molar ratio of 1:0.5, showed mostly normal glomerulus, protection of proximal and distal tubules and no infiltration of inflammatory cells.

Example 4

Captisol-MTX Time Studies

MTX-Captisol mixtures were administered as set forth in Table 4.

TABLE 4

| Treatment Single intravenous bolus injection via tail vein | | Tissue collection | MTX:Captisol molar ratio | Number of mice |
|---|---|---|---|---|
| Normal Mice | MTX 160 mg/kg | Kidney collected at 24 hrs | 1:0 | 4 |
| | MTX 160 mg/kg + captisol 764 mg/kg | | 1:1 | 4 |
| | MTX 160 mg/kg + captisol 382 mg/kg | after drug administration | 1:0.5 | 4 |
| | MTX 160 mg/kg + captisol 191 mg/kg | | 1:0.25 | 4 |
| Normal Mcie | MTX 160 mg/kg | Kidney collected at 48 hrs | 1:0 | 4 |
| | MTX 160 mg/kg + captisol 764 mg/kg | | 1:1 | 4 |
| | MTX 160 mg/kg + captisol 382 mg/kg | after drug administration | 1:0.5 | 4 |
| | MTX 160 mg/kg + captisol 191 mg/kg | | 1:0.25 | 4 |
| Normal Mice | MTX 160 mg/kg | Kidney collected after 1 week after drug administration | 1:1 | 4 |
| | MTX 160 mg/kg + captisol 764 mg/kg | | 1:1 | 4 |

For light microscopic investigation, kidneys were fixed in 10% buffered formalin and processed routinely for paraffin embedding. Tissue sections of 5 micron meter were stained with hematoxylin and eosine and examined under a Nikon coolpix light microscope, photography was done with a Nikon Coolpix camera. The severity of total kidney damage was evaluated by a semiquantitative measurement of damage as described below. Each tissue section of the kidney was assessed for degeneration of glomerular structure, glomerular crowding and congestion, dilation of bowman space, degeneration of proximal and distal tubules, and dilation of renal tubules, vascular congestion, and inflammatory cell infiltration. For glomerular atrophy, glomeruli that contained more than 20 nuclei were scored "0", and those containing less than 10 nuclei were scored "4." Intermediate stages were 1, 2 and 3. Other criterion was scored on a 0-3 scale: 0=none; 1=mild; 2=moderate; and 3=severe.

The microscopic score of each tissue was calculated as the sum of the scores given to each criterion and at least 100 nephrons (glomeruli plus surrounding tubules) were analyzed per section. See, e.g., Bhat et al., PNAS (2003) 100(7); Sener et al., *Cell Biol Toxicol* (2006) 22:470-60.

Figure 5:
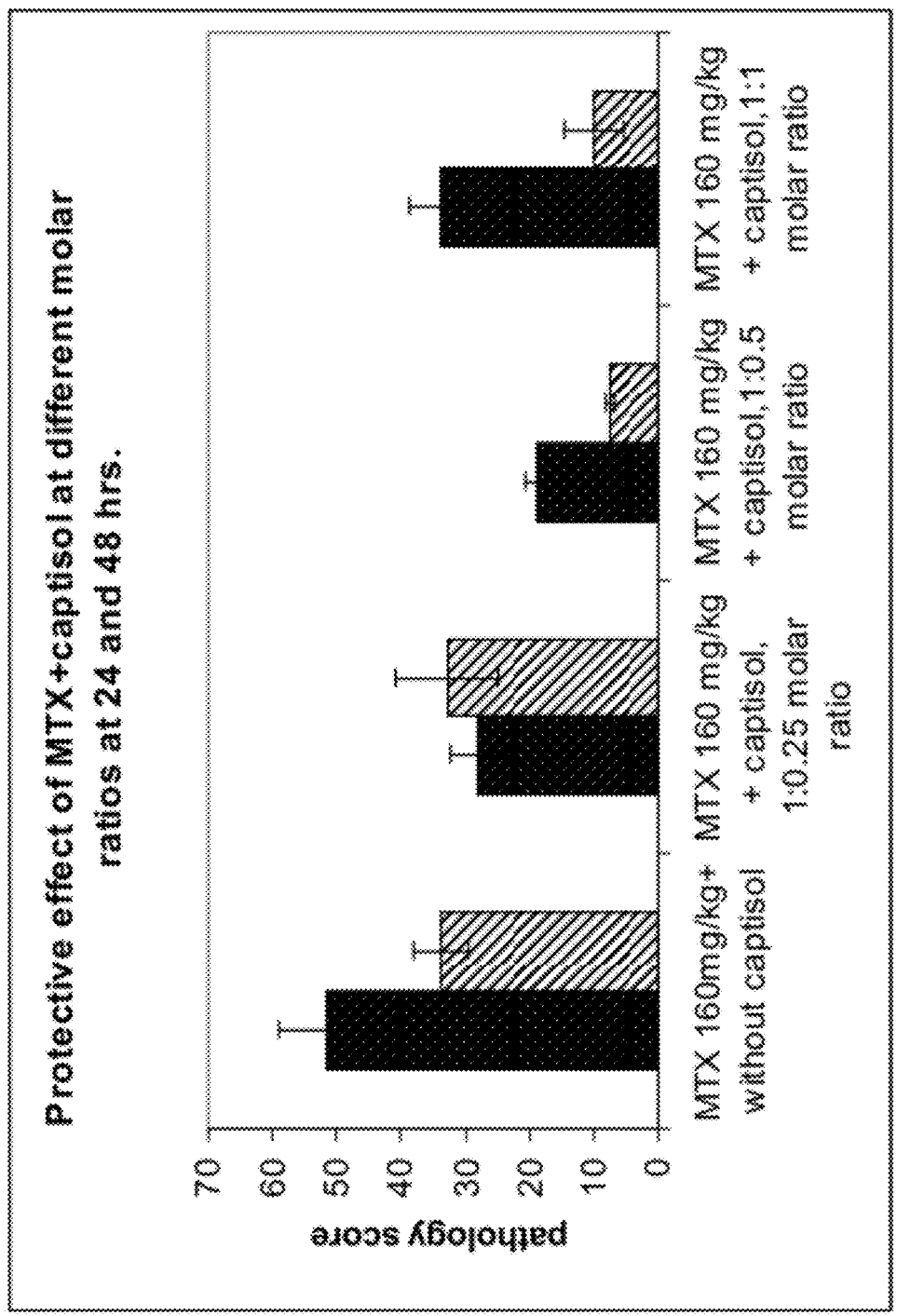
FIG. 5 shows renal pathology scores in the kidney tissue of mice 24 and 48 hours after treatment with MTX with or without concurrent captisol at different molar ratios.

Referring to FIG. 5, kidney tissue of MTX treated mice shows extensive histopathological changes after 24 and 48 hours. At 24 hours and 48 hours there was atrophy of the glomerulus, degeneration and dilation of Bowmans space, and inflammatory cell infiltration in the interstitium and tubular degeneration. The Captisol+MTX treated group showed milder glomerular and tubular changes and less infiltration of inflammatory cells. However, some of the changes seen after 24 hours appeared to be reversible since the cumulative pathological score was less at 48 hours compared to 24 hours.

Histopathological changes in the kidney were studied at 24 hours post MTX injection with or without captisol coadministration. Mice were sacrificed after 24 hours following MTX or MTX+Captisol coadministration. Paraffin sections of kidney were stained with hematoxylin and eosin (not shown). MTX 160 mg/kg administration resulted in degeneration of glomerular structure and dilation of Bowman's space, degeneration of proximal and distal tubules and inflammatory cell infiltration. Milder glomerular and tubular denegation was observed for MTX 160 mg/kg+Captisol at MTX to Captisol molar ratio of 1:1. MTX 160 mg/kg+Captisol at MTX to Captisol molar ratio of 1:0.5 were most effective in the preservation of glomerular and tubular structures. Infiltration of inflammatory cells was completely absent. MTX 160 mg/kg+Captisol used in molar ratio of 1:0.25 did not protect against kidney damage.

Histopathological changes were recorded for the kidney at 48 hours post MTX injection with or without Captisol coadministration. Mice were sacrificed after 48 hours following MTX or MTX+Captisol administration. Paraffin section of kidney were stained with hematoxylin and eosin (not shown). At 48 hours post injection, MTX 160 mg/kg administration (i.v.) resulted in degeneration of glomerular structure, dilation of Bowman's space, dilation of proximal and distal tubules, degeneration of proximal and distal tubules and inflammatory cell infiltration. Milder glomerular and tubular denegation was observed for MTX 160 mg/kg+Captisol (MTX to Captisol molar ratio of 1:1). MTX 160 mg/kg+Captisol in 1:0.5 molar ratio resulted in relatively better preservation of glomerular and tubular structure. Infiltration of inflammatory cells was completely absent. MTX 160 mg/kg+Captisol used in molar ratio of 1:0.25 were not effective in protecting the kidney from MTX induced damage. The greatest protection was seen when MTX to Captisol molar ratio was 1:0.5.

Histopathological changes were also studied for the kidney after 1 week post MTX administration. Mice were sacrificed after 1 week following MTX 160 mg/kg, single i.v. bolus injection. Paraffin sections of kidney were stained with hematoxylin and eosin (not shown). MTX administration alone resulted mainly in degeneration of proximal and distal tubules with occasional glomerular atrophy or crowding. Degenerating cells with swollen nuclei were seen lining the proximal and distal tubules. Occasionally some tubules were seen to be lined by double cell layer. Some tubules were congested with eosinophilic materials. The pathological changes were mostly found in the cortical areas of the kidney. Most of the glomerular structures were normal.

Histopathological changes were recorded for the kidney after 1 week post MTX+Captisol injection. Mice were sacrificed after 1 week following MTX+Captisol coadministration. Paraffin sections of kidney were stained with hematoxylin and eosin from four separate mice (not shown). Kidneys of mice coadministered with MTX 160 mg/kg+Captisol at MTX to Captisol molar ratio of 1:1 showed significantly less glomerular disruption and greater preservation of the tubules. Infiltration of inflammatory cells was absent.

Example 5

Evaluation of the Nephroprotective Effect of Captisol in Doxorubicin Induced Nephrotoxicity Model in Mice Female C57BL/6 mice were injected intravenously with a single dose of (10 mg/kg) doxorubicin. The mice were sacrificed after 72 hours. The development of glumerular and tubulointerstitial injury after doxorubicin and doxorubicin+Captisol was evaluated by means of renal histology. Paraffin sections of 5 µM were cut and stained with H&E and periodic acid Schiff (PAS). They were examined by light microscopy and scored in a blinded fashion. Thirty glomeruli and neighboring tubules were scored at superficial cortes (near the surface of the capsule). One hundred glomeruli and neighboring tubules were scored at the level of deep renal cortex and around the outer strips of the outer medulla.

Figure 6:
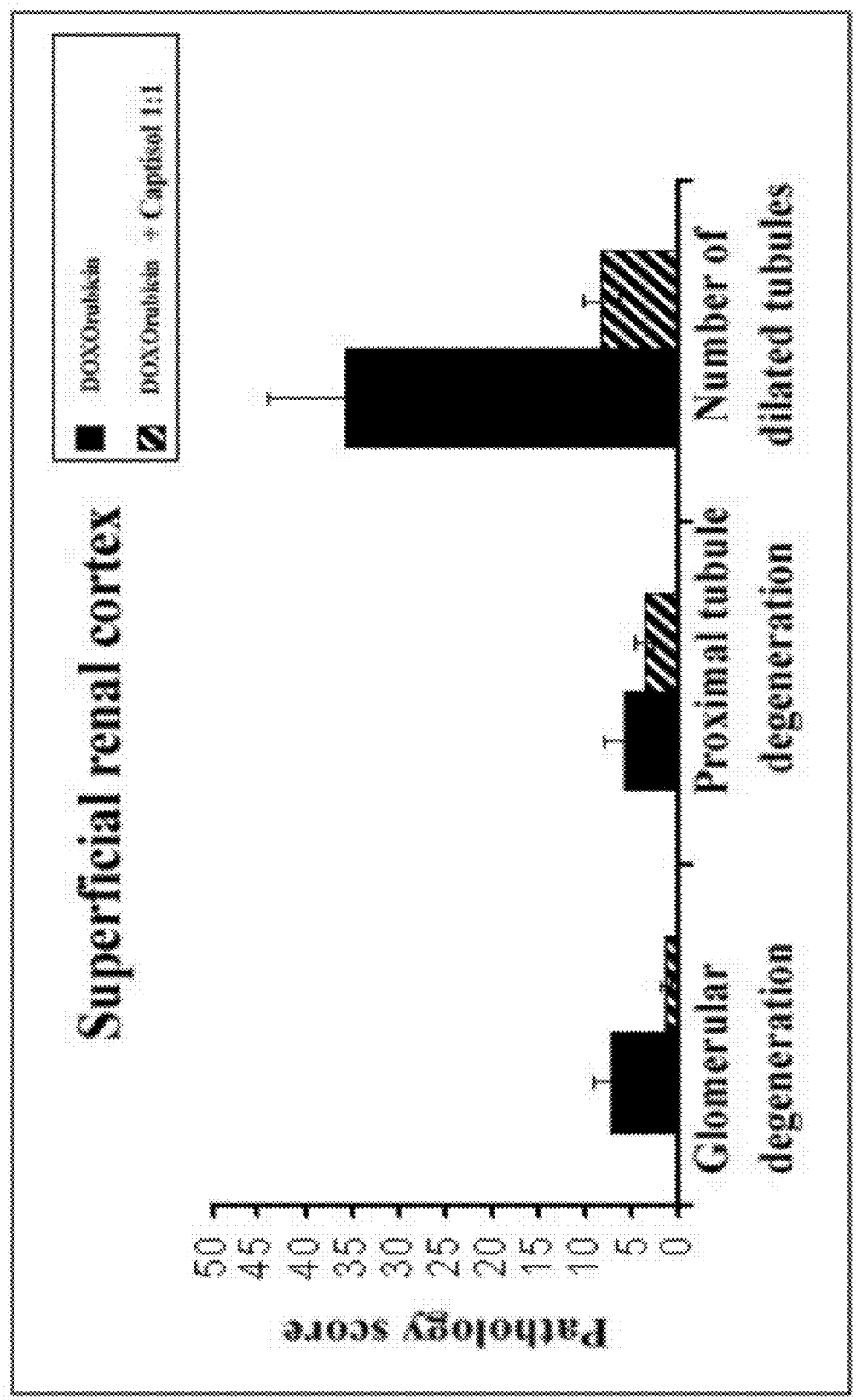
FIG. 6 shows the mean pathology scores in a doxorubicin induced nephrotoxic model for each treatment group at the level of superficial renal cortex.
Figure 7:
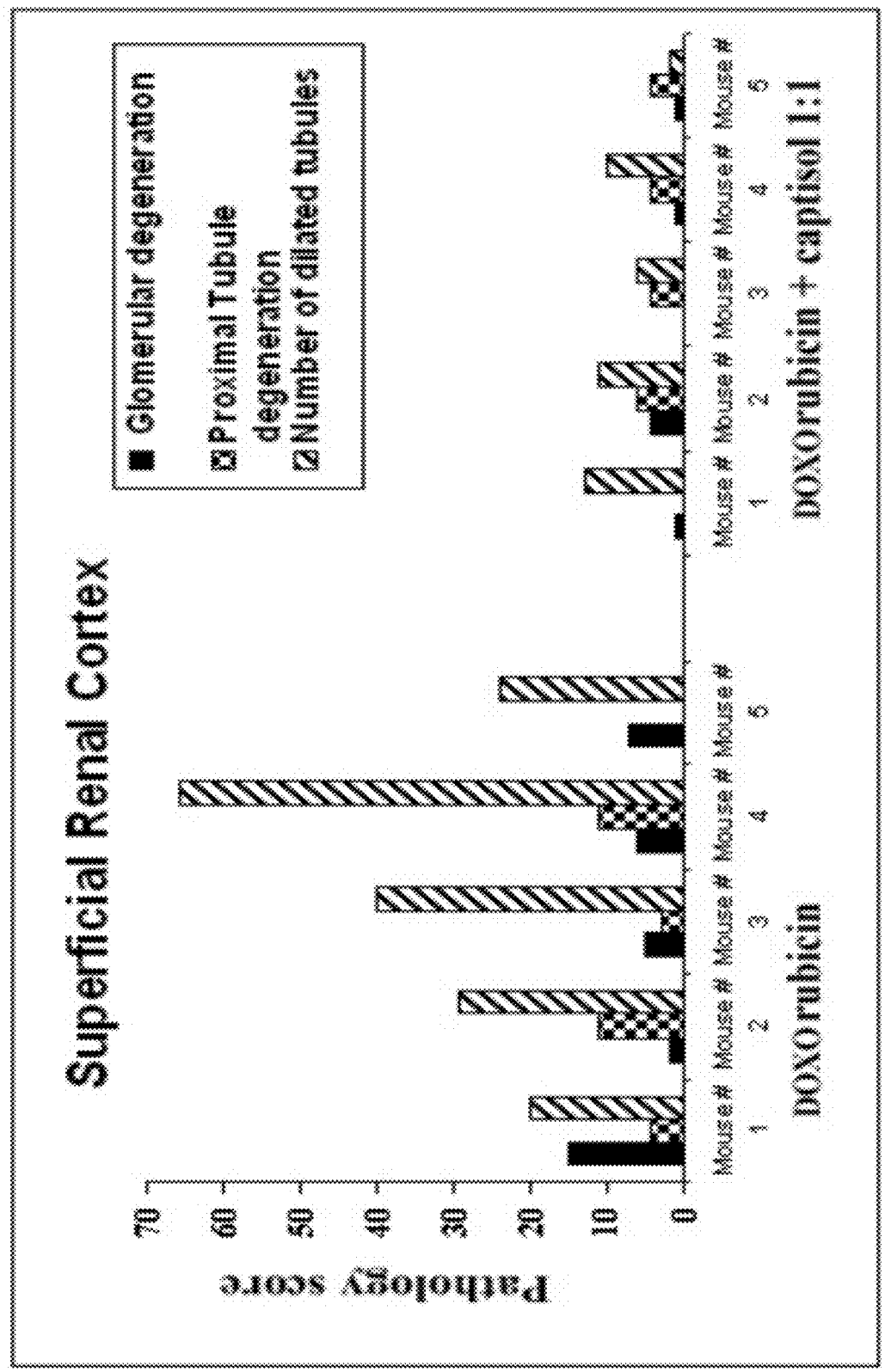
FIG. 7 shows the renal pathology scores for individual mice treated with doxorubicin or doxorubicin+captisol at the level of superficial renal cortex.
Figure 8:
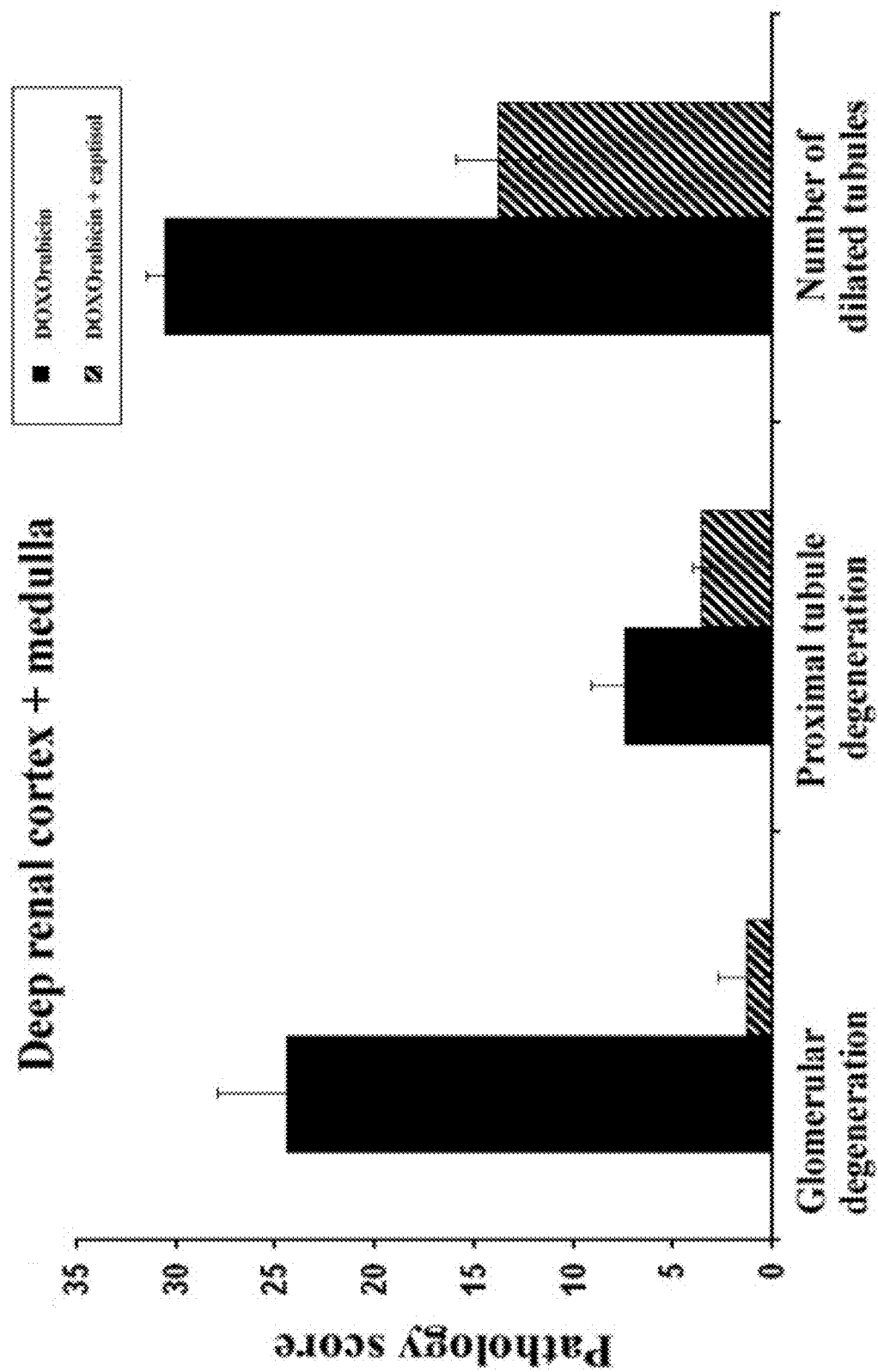
FIG. 8 shows the mean pathology scores in a doxorubicin induced nephrotoxic model for each treatment group at the level of deep renal cortex+outer medulla.
Figure 9:
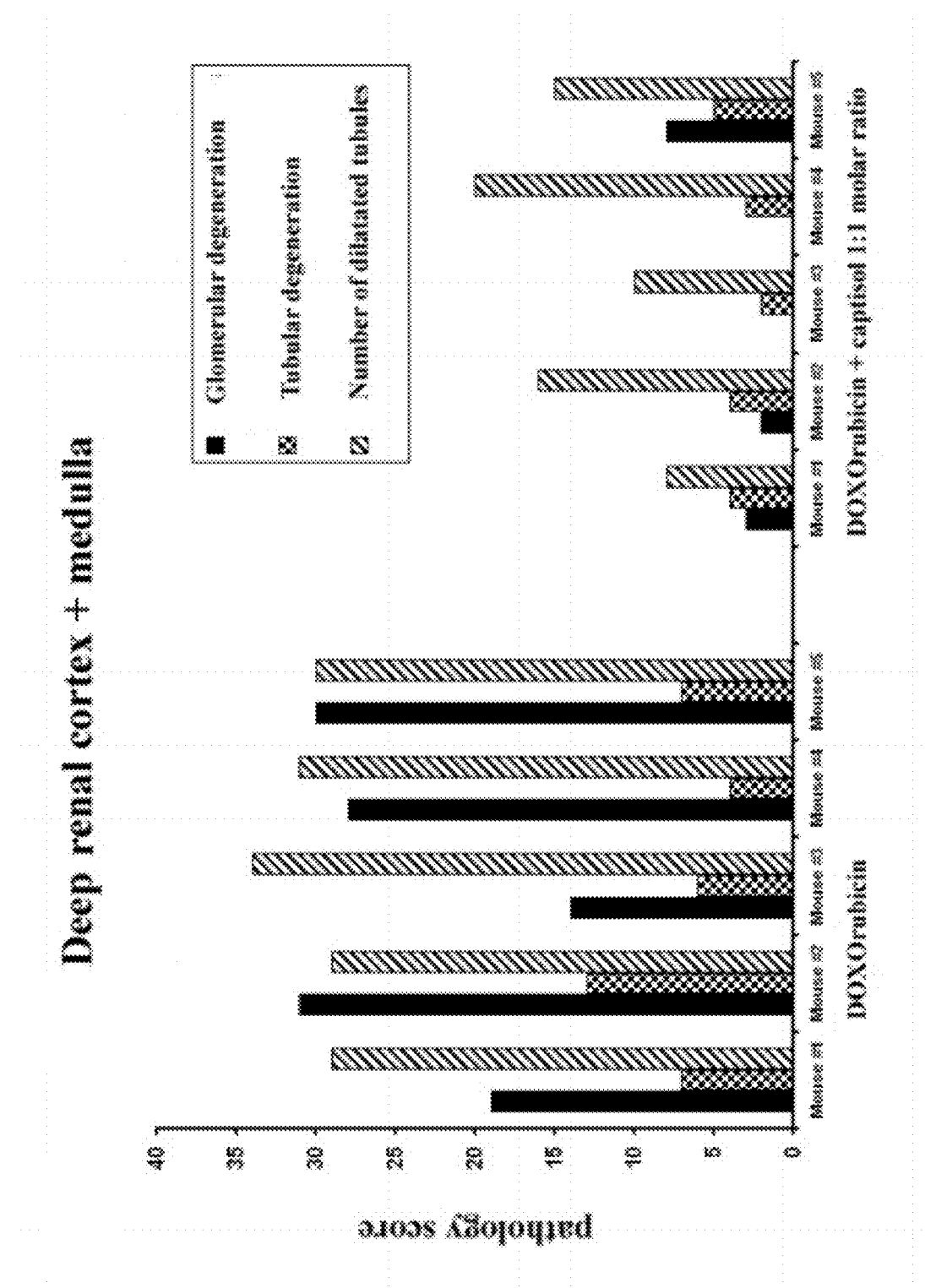
FIG. 9 shows the renal pathology scores for individual mice treated with doxorubicin or doxorubicin+captisol at the level of deep renal cortex+outer medulla.

FIG. 6 shows the mean pathology scores for each treatment group at the level of superficial renal cortex. FIG. 7 shows the renal pathology scores for individual mice treated with doxorubicin or doxorubicin+Captisol at the level of superficial renal cortex. FIG. 8 shows the mean pathology scores for each treatment group at the level of deep renal cortex+outer medulla. FIG. 9 shows the renal pathology scores for individual mice treated with doxorubicin or doxorubicin+Captisol at the level of deep renal cortex+outer medulla.

None of the control or Captisol treated mice had any tubulointerstitial changes. The doxorubicin treated group showed tubular casts, abundant dilated tubules and moderate loss of brush border in the some proximal tubules. Some of the glomeruli were collapsed and at various stages of degeneration. The pathology was found to be more prominent in the outer periphery of the renal cortex. Tubular atrophy or neutrophils infiltration was not seen. In doxorubicin+captisol treated mice there was almost 71% reduction of degeneration and almost 72% reduction in tubular dilatation. At deeper renal cortex and medulla, there was a 90% reduction in glomerular degeneration and a 50% reduction in tubular dilatation.

Example 6

Evaluation of the Nephroprotective Effect of Captisol in Cisplatin Induced Nephrotoxicity Model in Mice Female C57BL/6 mice were injected intravenously with a single dose of (10 mg/kg) cisplatin (N=5) or cisplatin+Captisol at cisplatin to Captisol molar ratio of 1:1, 1:0.5 and 1:0.25 (N=5, N=4 and N=6, respectively). The animals were sacrificed after 72 hours.

The development of glumerular and tubulointerstitial injury after cisplatin and protection by cisplatin+Captisol was evaluated by means of renal histology. Paraffin sections of 5 μM were cut and stained with H&E and periodic acid Schiff (PAS). They were examined by light microscopy and scored in a blinded fashion. Thirty glomeruli and neighboring tubules were scored at the superficial cortex (near the surface of the capsule). One hundred glomeruli and neighboring tubules were scored at the level of deep renal cortex and around the outer strips of the outer medulla.

Figure 10:
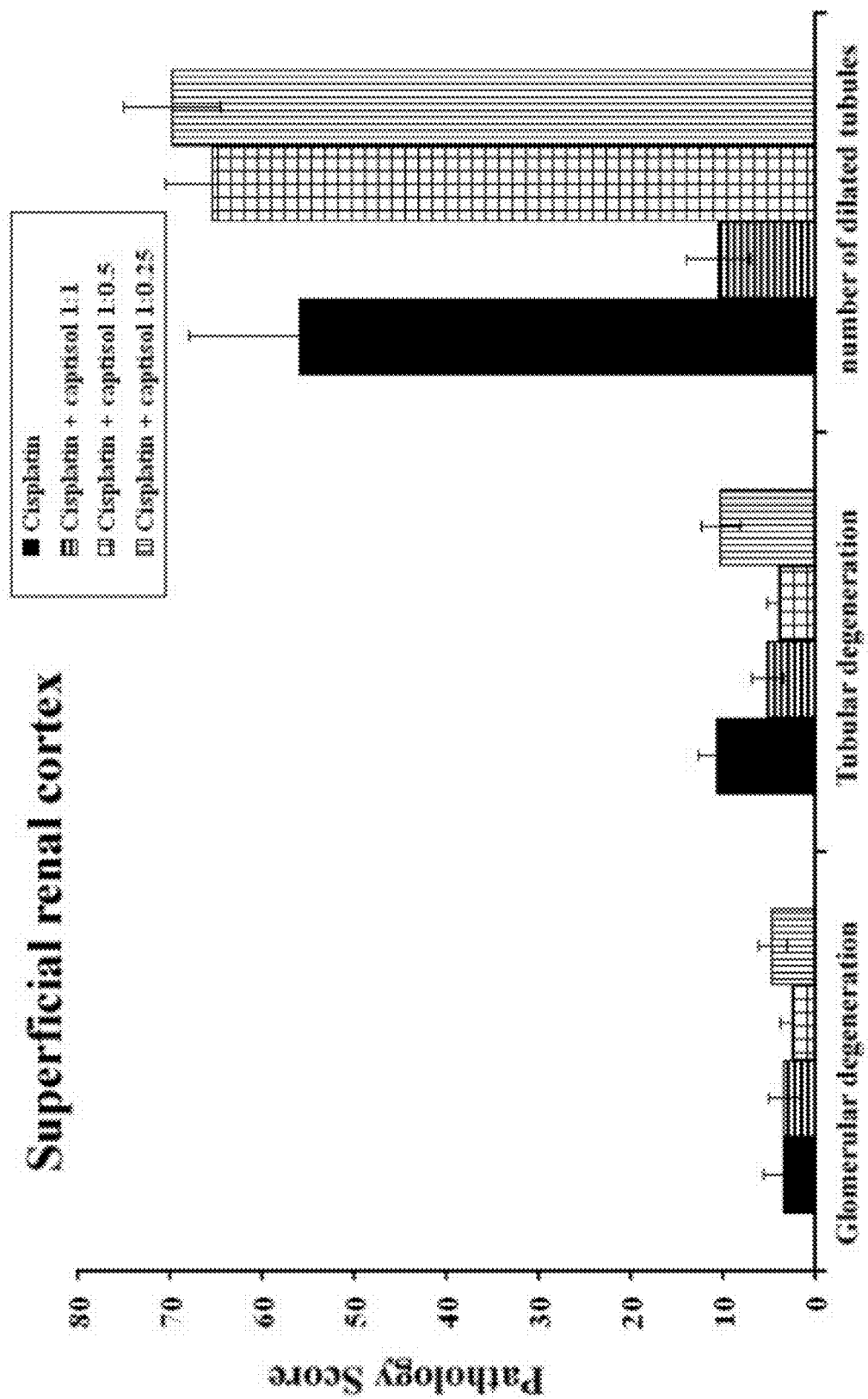
FIG. 10 shows the mean scores at the level of the superficial cortex in cisplatin and cisplatin+captisol treated groups.
Figure 11:
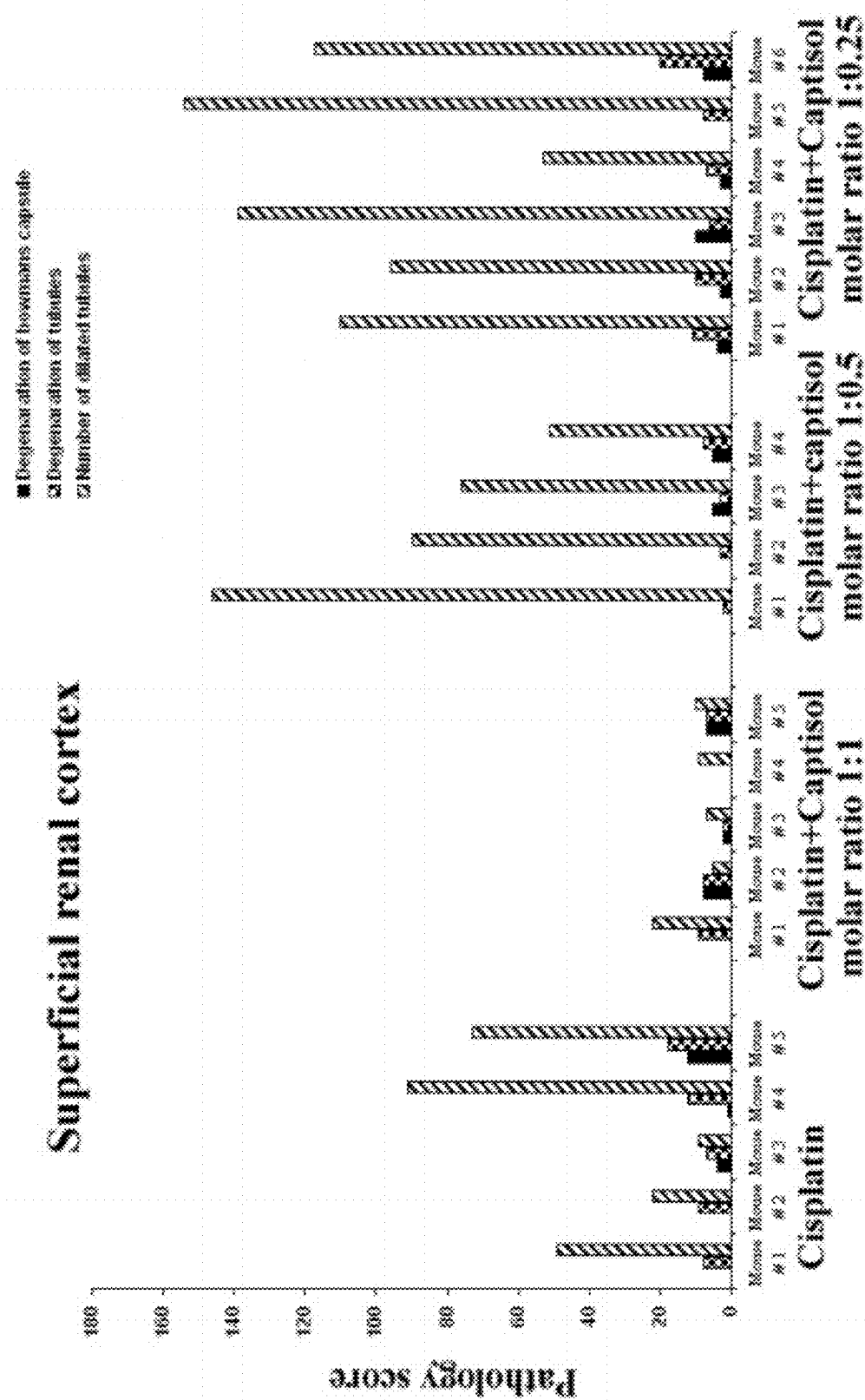
FIG. 11 shows the pathology scores in a cisplatin induced nephrotoxic model of individual mice in each treatment group at the level of the superficial renal cortex.
Figure 12:
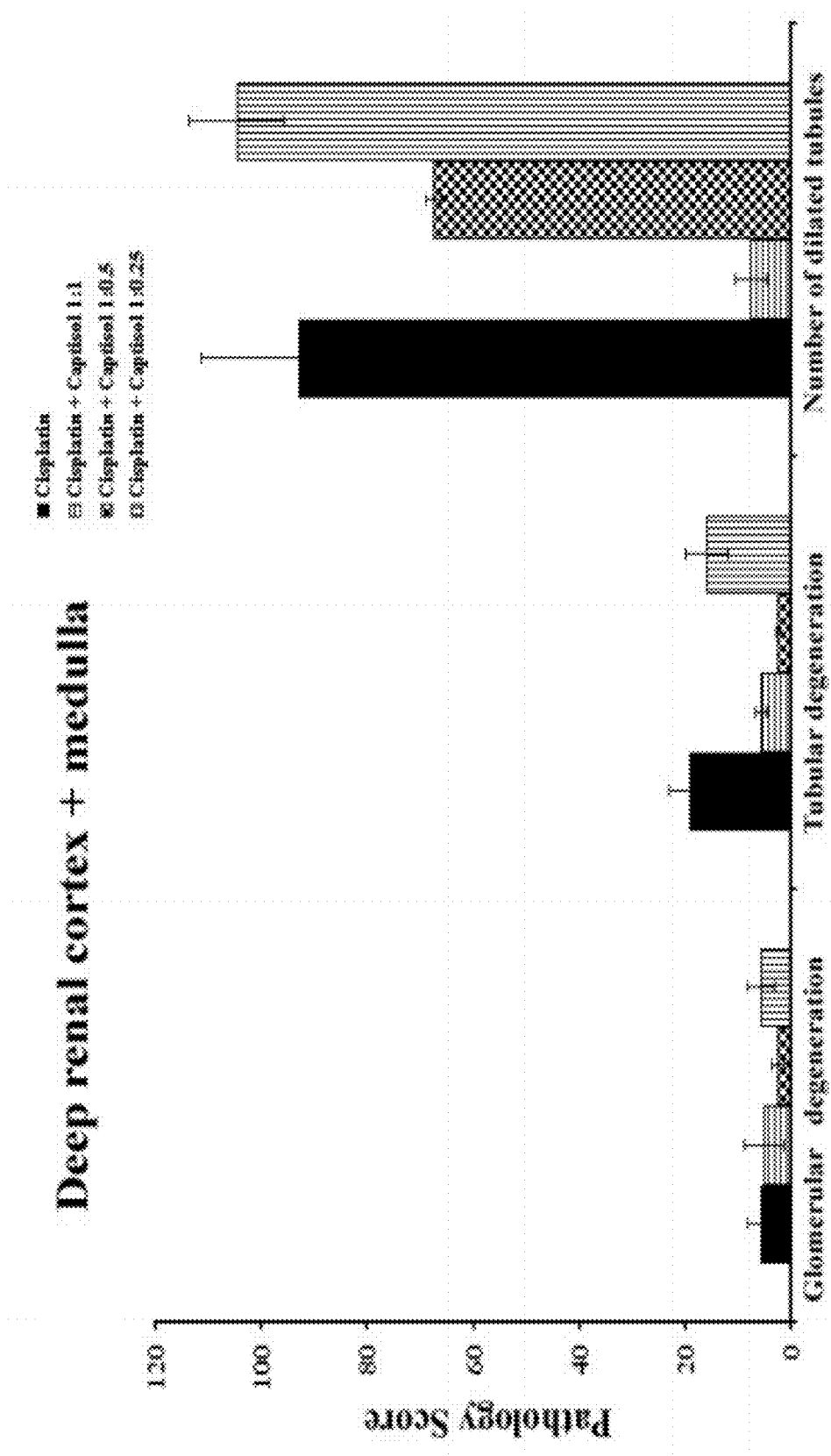
FIG. 12 shows the mean scores at the level of the deep cortex and outer medulla in cisplatin and cisplatin+captisol treated groups.
Figure 13:
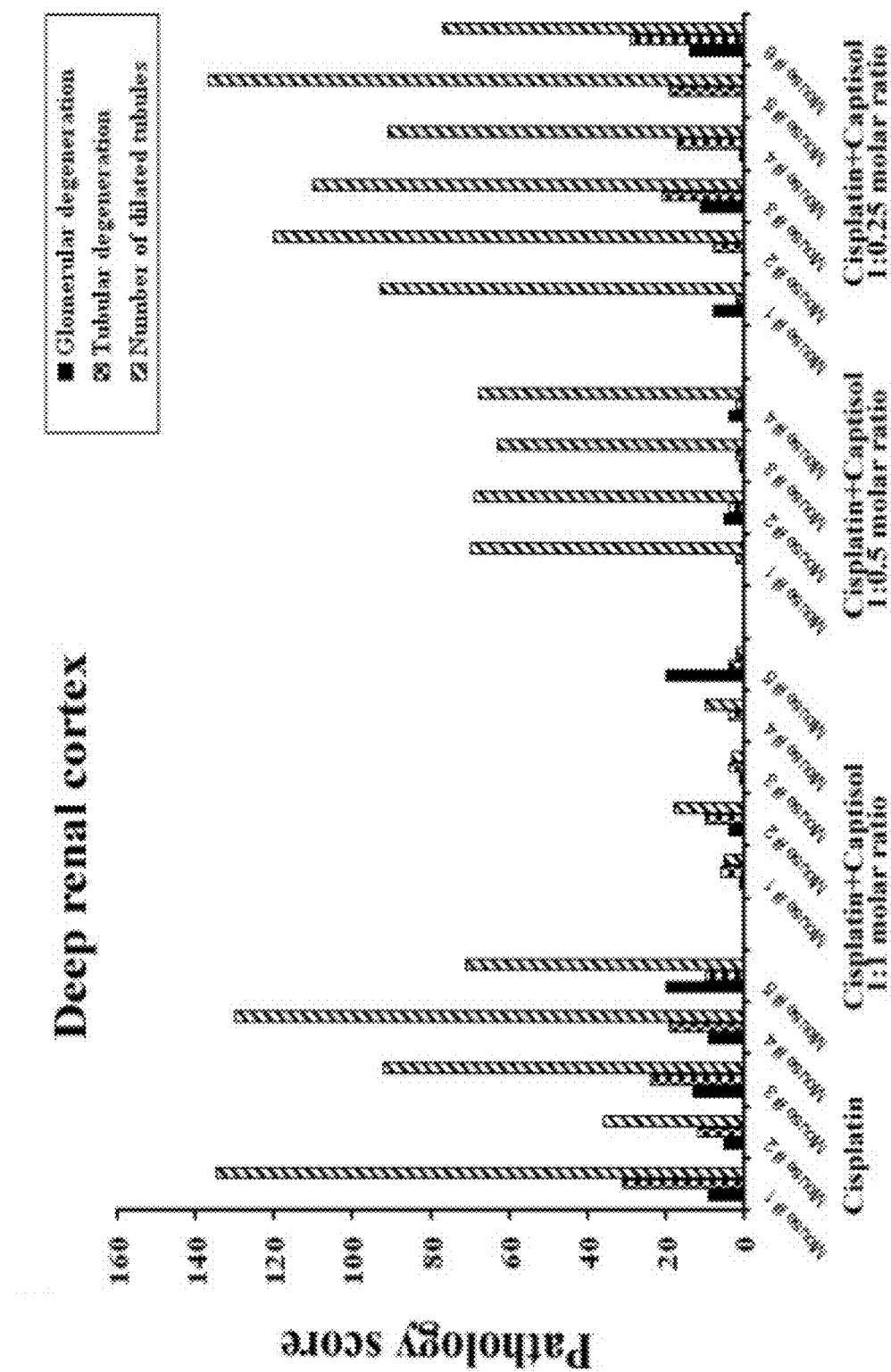
FIG. 13 shows pathology scores in a cisplatin induced nephrotoxic model of individual mice in each treatment group at the level of the deep renal cortex and outer medulla.
Figure 14:
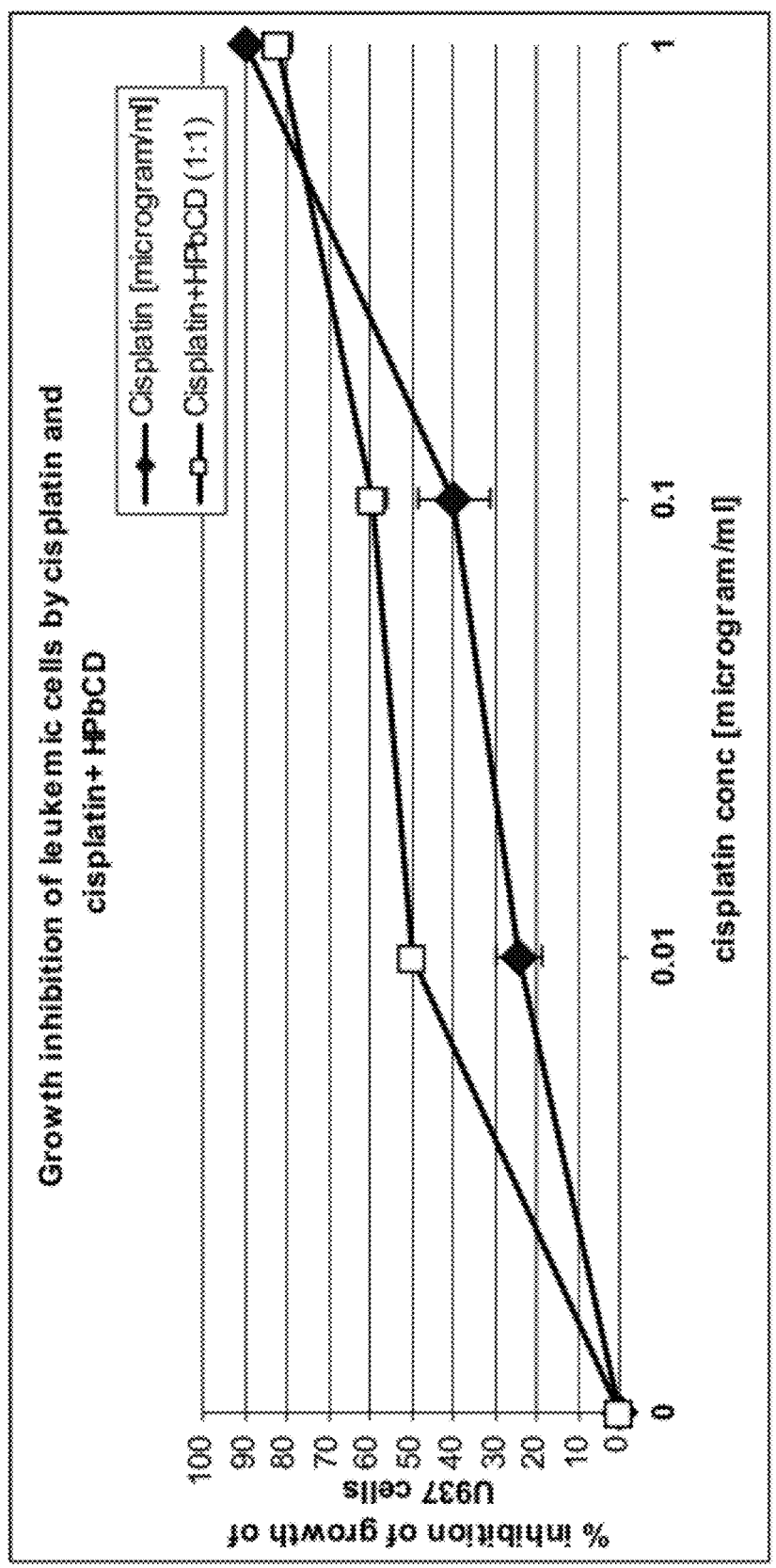
FIG. 14 shows a comparison of the effect of cisplatin/HPβCD and cisplatin alone on the growth of leukemia cells.

FIG. 10 shows the mean scores at the level of the superficial cortex in cisplatin and cisplatin+Captisol treated groups (cisplatin to Captisol molar ratio 1:1, 1:0.5 and 1:0.25). FIG. 11 shows the pathology scores of individual mice in each treatment group at the level of the superficial renal cortex. FIG. 12 shows the mean scores at the level of the deep cortex and outer medulla in cisplatin and cisplatin+Captisol treated groups (cisplatin to Captisol molar ratio 1:1, 1:0.5 and 1:0.25). FIG. 13 shows pathology scores of individual mice in each treatment group at the level of the deep renal cortex and outer medulla.

None of the control mice had any tubulointerstitial changes. The cisplatin treated mice showed necrosis, sloughing of tubular epithelial cells and loss of brush border in the some proximal tubules. Abundant presence of dilated tubules was a prominent feature of cisplatin induced nephrotoxicity. Some of the glomeruli were collapsed and some showed early degenerative changes. All of these changes were significantly less pronounced by treatment with cisplatin+Captisol, demonstrating that Captisol protected the kidney at both cisplatin:Captisol 1:1 and cisplatin:Captisol 1:0.5.

Example 7

Nephroprotective Effect of SBE-βCD in Gentamicin Induced Nephrotoxicity in Mice

Earlier studies have shown that gentamicin administration at clinically relevant doses failed to produce measurable toxicity in mice. These doses however, produce nephrotoxicity in humans. Therefore, nephroprotective effects of SBE-βCD in mildly renal compromised mice was evaluated. These mice were shown to exhibit pathological changes in the kidney in clinically relevant doses. In order to produce mildly renal compromised mice, animals were injected with L-NAME (L arginine methyl ester) 10 mg/kg and Indomethacin 10 mg/kg, ip., 15-20 min before the first injection of gentamicin. Female C57BL/6 mice were administered bolus intravenous injections for ten consecutive days with a dose of 4.0 mg/kg gentamicin (N=4) or gentamicin 4.0 mg/kg+SBE-βCD 19.2 mg/kg (N=4), or gentamicin 4.0 mg/kg+SBE-βCD 38.4 mg/kg (N=4). Gentamicin to SBE-βCD molar ratios were 1:1 and 1:2 respectively. Animals were sacrificed after 48 hrs after the last injection. Renal pathology was assessed by evaluating H&E sections of the kidney under light microscope. Experimental details are given in Table 5 below.

TABLE 5

| Groups | Protocol | Days of injection | G:C molar ratio |
|---|---|---|---|
| C57BL6 Mice (female) N = 5 Mildly renal compromised mice | Gentamicin 4.0 mg/kg, administered iv. via tail vein. Bolus injections were made. | 10 consecutive days. Mice were sacrificed 72 hrs later. | Without SBE-βCD |
| C57BL6 Mice (female) N = 2 Healthy mice (not renal compromised) | Gentamicin 4.0 mg/kg, administered iv. via tail vein. Bolus injections were made. | 10 consecutive days. Mice were sacrificed 72 hrs later | Without SBE-βCD |
| C57BL6 Mice (female) N = 4 Mildly renal compromised mice | Gentamicin 4.0 mg/kg + SBE-βCD 19.22 mg/kg together, administered concurrently, iv. via tail vein. Bolus injection. | 10 consecutive days. Mice were sacrificed 72 hrs later. | Gentamicin:SBE-βCD molar ratio 1:1 |
| C57BL6 Mice (female) N = 4 Mildly renal compromised mice | Gentamicin 4.0 mg/kg + SBE-βCD 38.4 mg/kg, concurrently, administered iv. | 10 consecutive days. Mice were sacrificed 72 hrs later. | Gentamicin:SBE-βCD molar ratio 1:2 |

Paraffin sections of 5 μM were cut and stained with H&E and periodic acid Schiff (PAS). They were examined by light microscopy and scored in a blinded fashion. Five arbitrary fields at 40× magnification in each sections was assessed for the below mentioned parameters and scored according to the criteria mentioned Dilated Tubules
0=Normal, no dilated tubules
1=mild, 1-2 dilated tubules
2=moderate, 3-5 dilated tubules
3=Severe, 6-8 dilated tubules
4=extremely severe, more than 8 dilated tubules
Tubular Casts
0=casts absent
1=mild, 1-2 casts per field
2=moderate, 3-5 casts per field
3=severe, 6-8 casts per field
4=extreme, more than 8 casts per field
Vacuoles
0=Normal, no vacuoles
1=mild, 1-4 vacuoles
2=moderate, 5-8 vacuoles
3=Severe, 9-12 vacuoles
4=extremely severe, 13-16 vacuoles
Tubular Degeneration
0=none,
1=mild, up to 25% of the visual field has degenerating tubules
2=moderate, up to 50% of the visual field has degenerating tubules
3=severe, up to 75% of the visual field has degenerating tubules
4=Extreme, more than 75% of the visual field has degenerating tubules
Inflammation
0=Normal, No inflammatory cells were seen
1=mild, up to 25% of the visual field covered with inflammatory cells
2=moderate, up to 50% of the visual field covered with inflammatory cells
3=Severe, up to 75% of the visual field covered with inflammatory cells
4=extremely severe, more than 75% of the visual field covered with inflammatory cells
Edema
0=none
1=mild
2=moderate
3=severe, 4=extreme Under the present conditions, low dose gentamicin (4 mg/kg) given intravenously induced no noticeable changes in the tubular cells in the healthy kidney. However, when the mice were mild renal compromised, gentamicin at 4 mg/kg produced extensive tubular vacuolization and necrosis in the renal cortex; the tubular cells were flattened and partly discontinuous, and the lumens were widened. There was no noticeable alteration the distal tubules, collecting ducts and the glomerulus.

The combination of gentamicin with SBE-βCD in a molar ratio of 1:1 and 1:2 offered significant protection against gentamicin induced nephrotoxicity. The reduction in kidney pathology as a mean of all 6 evaluation parameters was approximately 62%. There was attenuation of tubular dilation and proximal tubule vacuolization, and tubular cast formation, as well as a reduction in tubular necrosis, and infiltration of mononuclear cells. The effect of SBE-βCD was dose dependent, and the 1:2 mole ratio of gentamicin to SBE-βCD was more effective than the 1:1 mole ratio for most of the individual parameters.

Example 8

Nephroprotective Effect of SBEβCD in Acyclovir Induced Nephrotoxicity in Mice

Earlier studies have shown that acyclovir administration at clinically relevant doses failed to produce measurable toxicity in mice. These doses however, produce nephrotoxicity in humans. Therefore, the nephroprotective effects of sulfobutylether β cyclodextrin (SBEβCD) in mildly renal compromised mice was evaluated. These mice were shown to exhibit pathological changes in the kidneys in clinically relevant doses of acyclovir. In order to produce mildly renal compromised mice, animals were injected with L-NAME (L arginine methyl ester) 10 mg/kg and Indomethacin 10 mg/kg, ip., 15-20 min before the first injection of acyclovir. Female C57BL/6 mice were administered bolus intravenous injections for ten consecutive days with a dose of 10 mg/kg acyclovir (N=3) or acyclovir 10 mg/kg+SBEβCD 173 mg/kg (N=3), or 30 mg/kg acyclovir (N=3) or acyclovir 30 mg/kg+SBEβCD 520 mg/kg (N=3) (Table 6). In both cases the acyclovir to SBEβCD molar ratio was 1:2. Animals were sacrificed after 48 hrs after the last injection. Renal pathology was assessed by evaluating H&E sections of the kidney under a light microscope.

TABLE 6

| Acyclovir dose/regimen | Acyclovir [Molarity] | SBEβCD dose & regimen | SBEβCD [molarity] | Acyclovir:SBEβCD molar ratio | Kidney collection |
|---|---|---|---|---|---|
| 10.0 mg/kg, IV, for 10 consecutive days (n = 3) | 4.0 mM | 0.0 | 0.0 | N/A | 48 hrs. after the last injection |
| 10.0 mg/kg, IV, for 10 consecutive days (n = 3) | 4.0 mM | 173 mg/kg [8.0 mM], concurrently | 8.0 mM | 1:2 | 48 hrs. after the last injection |
| 30.0 mg/kg, IV, for 10 consecutive days (n = 3) | 12.1 mM | 0.0 | 0.0 | N/A | 48 hrs. after the last injection |

TABLE 6-continued

| Acyclovir dose/regimen | Acyclovir [Molarity] | SBEβCD dose & regimen | SBEβCD [molarity] | Acyclovir:SBEβCD molar ratio | Kidney collection |
|---|---|---|---|---|---|
| 30.0 mg/kg, IV, for 10 consecutive days (n = 3) | 12.1 mM | 520.0 mg/kg [24.2 mM], concurrently | 24.2 mM | 1:2 | 48 hrs. after the last injection |

Paraffin sections of 5 μM were cut and stained with H&E and periodic acid Schiff (PAS). They were examined by light microscopy and scored in a blinded fashion. Five arbitratary fields at 40× magnification in each sections was assessed according to the below mentioned parameters and scored according to the criteria mentioned.

Dilated Tubules
0=Normal, no dilated tubules
1=mild, 1-2 dilated tubules
2=moderate, 3-5 dilated tubules
3=Severe, 6-8 dilated tubules
4=extremely severe, more than 8 dilated tubules Vacuoles
0=Normal, no vacuoles
1=mild, 1-4 vacuoles
2=moderate, 5-8 vacuoles
3=Severe, 9-12 vacuoles
4=extremely severe, 13-16 vacuoles Inflammation
0=Normal, No inflammatory cells were seen
1=mild, up to 25% of the visual field covered with inflammatory cells
2=moderate, up to 50% of the visual field covered with inflammatory cells
3=Severe, up to 75% of the visual field covered with inflammatory cells
4=extremely severe, more than 75% of the visual field covered with inflammatory cells Increase in the Number of Tubular Cells
0—absent
1=mild, up to 25% of the tubules have increased cell numbers or overlapping of cells
2=moderate, up to 50% of the tubules have increase cell numbers or overlapping of cells
3=Severe, up to 75% of the tubules have increased cell numbers or overlapping of cells
4=extremely severe, more than 75% of the visual field covered with inflammatory cells Chronic administration of acyclovir in mildly renal compromised mice caused a dose dependent increase in pathological changes in the morphology of the kidney. Acyclovir treatment produced moderate to severe signs of tubulopathy as indicated by numerous dilated tubules and irregular vacuolization of the proximal tubular epithelium. Other signs of tubular damage were absent, such as microcalcification or necrosis of epithelial cells. Mild infiltration of mononuclear cells was seen in the parenchyma. Most of the pathology, in particular tubular dilation, was seen along the periphery of the cortex. Glomerular pathology was minimal.

Concurrent administration of SBEβCD in a molar ratio of 1:2 resulted in significant attenuation of tubular dilation and vacuole formation in the tubules in both the outer cortex and in the medulla. In addition, there was attenuation in tubular casts and infiltration of mononuclear cells within the parenchyma. The reduction in kidney pathology as a mean of the several parameters evaluated was 62% for the 30 mg/kg dose of acyclovir and 67% for the 10 mg/kg dose.

Example 9

Nephroprotective Effect of SBE-βCD in Iohexyl Induced Nephrotoxicity in Mice

Iohexyl is nephrotoxic in humans and can produce acute renal failure in renally compromised patients. Therefore, the nephroprotective effects of sulfobutyl ethyl β cyclodextrin (SBE-βCD) in a contrast agent induced nephropathy model involving mildly renal compromised mice was evaluated. These mice were shown to develop pathological changes in the kidney in clinically relevant doses of iohexyl. In order to produce mildly renal compromised mice, female C57BL/6 mice were injected with nitric oxide synthase inhibitor L-NAME (L arginine methyl ester) 10 mg/kg and prostaglandin synthesis inhibitor Indomethacin 10 mg/kg, ip., 15-20 min before injecting of iohexyl. The mice were administered a single bolus intravenous injections of iohexyl 1.5 g/kg (N=4) or iohexyl 1.5 g/kg+SBE-βCD 1.3 g/kg (N=4), or iohexyl 1.5 g/kg+SBE-βCD 1.3 mg/kg administered 30 minutes before, concurrently, and 30 min after iohexyl injection (N=4) (Table 7). In both cases, the iohexyl to SBE-βCD molar ratio was 1:0.1 during the concurrent dose. However, in the second case the molar concentration in vivo is expected to be higher. Animals were sacrificed 24 hrs after the iohexyl injection. Renal pathology was assessed by evaluating H&E sections of the kidney under a light microscope.

TABLE 7

| Iohexol dose/regimen | Iohexol [Molarity] | SBE-βCD dose & regimen | I:SBE βCD molar ratio | Kidney collection |
|---|---|---|---|---|
| 1.5 g/kg, iv., once (n = 4) | 423 mM | 0.0 | 0.0 | 24 hrs. after Iohexol injection |
| 1.5 g/kg, iv., once (n = 4) | 423 mM | 1.3 g/kg, [141.9 mM], concurrently | 1:0.1 | 24 hrs. after Iohexol injection |
| 1.5 g/kg, iv., once (n = 4) | 423 mM | 1.3 g/kg each, 3 doses, given 30 min before, during, and 30 min after Iohexol injection | 1:0.1 (for the concurrent dose) | 24 hrs. after Iohexol injection |

Paraffin sections of 5 μM were cut and stained with H&E and periodic acid Schiff (PAS). They were examined by light microscopy and scored in a blinded fashion. At 40× magnification, five arbitrary fields in each section was assessed for the below mentioned parameters and scored blindly according to the criteria mentioned. A total of 4 sections were analyzed per kidney.

Administration of the contrast agent iohexyl in mildly renal-compromised mice caused pathological changes in the morphology of the kidney tubules. Iohexyl treatment produced moderate to severe signs of tubulopathy as indicated by the presence of numerous dilated tubules, tubular casts, vacuolization of the proximal tubular epithelium, and degeneration of proximal tubules. Other signs of tubular damage were absent, such as basophilia, microcalcification or necrosis of epithelial cells. Most of the pathology, in particular tubular dilation, was seen along the periphery of the cortex. The majority of the glomeruli appeared normal.

The concurrent administration of SBE-βCD with iohexyl to SBE-βCD at a molar ratio of 1:0.1 resulted in significant attenuation of tubular dilation, tubular cast formation, and vacuolization of the tubular epithelium in both the outer cortex and the medulla. The protective effect of SBE-βCD appeared to be enhanced when it was given in 3 doses (once before, during and after iohexyl injection). However, an increase in vacuolization was seen in these mice which could be due to a high local concentration of SBE-βCD achieved in the mouse kidney. Higher doses of SBE-βCD (in mice) have been shown to produce reversible vacuolization of the proximal tubules. Even though 1.3 g/kg is below what is expected to produce vacuolization in mice, the cumulative dose may have been higher. The reduction in kidney pathology score as a mean of the several parameters evaluated was approximately 72% when the SBE βCD was given in one dose concurrently with the iohexyl.

Example 10

Nephroprotective Effect of HPβCD in a Methotrexate Induced Nephrotoxicity Model in Mice To determine the protective effect of other cyclodextrin molecules, 2-hydroxypropyl β-cyclodextrin (HPβCD) was evaluated. Female C57BL/6 mice were injected intravenously with a single dose of methotrexate 80 mg/kg, IV, or methotrexate+HPβCD, IV, at methotrexate to HPβCD molar ratios of 1:1 and 1:0.5. The animals were sacrificed after 24 hrs. The development of glomerular and tubulointerstitial injury after methotrexate and protection by methotrexate+HPβCD was evaluated by means of assessment of renal histology by light microscopy. Leukovorin was given 4 hrs and after 18 hrs. Urine was not alkalinized.

Paraffin sections of 5 μM were cut and stained with H&E and periodic acid Schiff (PAS). They were examined by light microscopy and scored in a blinded fashion. Five arbitratary fields at 40× magnification in each sections was assessed for the parameters, and scored according to the criteria, set forth in Example 7.

In normal mice a single IV injection with MTX at 80 mg/kg produced significant histopathological changes in the kidney in the form of mildly atrophied glomeruli, tubular degeneration, cast formation, dilation and infiltration of mononuclear cells. In mice treated concurrently with MTX+HPβCD (with both 1:1 and 1:05 molar ratios) there was significant reduction in tubular pathology and better preservation of glomerular structure was seen. Overall MTX:HPβCD molar ratio of 1:0.5 was more effective than a molar ratio of 1:0.05. The reduction in kidney pathology as a mean of the several parameters measured was approximately 55%.

I claim:

1. A method of inhibiting or reducing nephrotoxicity associated with an iodinated contrast agent, the method comprising:
administering to a subject in need thereof a first pharmaceutical composition comprising an anionically substituted cyclodextrin of the formula:

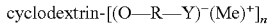

cyclodextrin-[(O—R—Y)⁻(Me)⁺]$_n$ where R is selected from the group consisting of straight chained or branched $C_{1-10}$ alkyl, alkenyl or alkynyl;
Y is an anionic group selected from COO, $SO_3$, $SO_4$, $PO_3H$ or $PO_4$;
Me is a pharmaceutically acceptable cation; and
n is a whole number greater than 1, and
administering to the subject a second pharmaceutical composition comprising an iodinated contrast agent selected from iohexyl, ioversol, diatrizoate meglumine and ioxaglate; wherein the molar ratio of agent: cyclodextrin is from 2:1 to 50:1.

2. The method of claim 1, wherein the first pharmaceutical composition further comprises a pharmaceutically acceptable carrier, the second pharmaceutical composition further comprises a pharmaceutically acceptable carrier, or both the first and second pharmaceutical compositions further comprise a pharmaceutically acceptable carrier.

3. The method of claim 1 wherein the iodinated contrast agent is iohexyl.

4. The method of claim 1 wherein said cyclodextrin is β-cyclodextrin, (O—R—Y)⁻(Me)⁺ is —O—$(CH_2)_4$—$SO_3^-$ $Na^+$, and n is about 7.

5. The method of claim 1, wherein R is $C_{1-4}$ alkyl selected from methyl, ethyl, propyl and butyl.

6. The method of claim 1, wherein R is butyl.

7. The method of claim 1, wherein Y is $SO_3$.

8. The method of claim 7 wherein said cyclodextrin is selected from one or more of the group consisting of α, β and γ cyclodextrin.

9. The method of claim 1 wherein the administering of the first pharmaceutical composition is performed over any period of time selected from within one hour before to within one hour after administering the second pharmaceutical composition.

10. The method of claim 9 wherein the administering of the first pharmaceutical composition is performed concurrently with the administering of the second pharmaceutical composition.

11. The method of claim 1, wherein the administering of the first pharmaceutical composition is performed over any period of time selected from within 30 minutes before to concurrently with the second pharmaceutical composition.

12. The method of claim 1, wherein the administering of the first pharmaceutical composition is performed over any period of time selected from concurrently to within 30 minutes after administering the second pharmaceutical composition.

13. The method of claim 1, wherein the administering of the first pharmaceutical composition is performed in three doses, the first dose administered over a period of time within 30 minutes before the second pharmaceutical composition, the second dose administered concurrently with the second pharmaceutical composition, and the third dose administered over a period of time within 30 minutes after administering the second pharmaceutical composition, and wherein the molar ratio of agent:cyclodextrin is from 2:1 to 50:1 when the first and second pharmaceutical compositions are administered concurrently.

* * * * *

UNITED STATES PATENT AND TRADEMARK OFFICE
CERTIFICATE OF CORRECTION

PATENT NO.         : 8,574,551 B2                                                Page 1 of 1
APPLICATION NO.    : 13/592510
DATED              : November 5, 2013
INVENTOR(S)        : Rowe It is certified that error appears in the above-identified patent and that said Letters Patent is hereby corrected as shown below:

In the Specification
In column 9, line 29, delete "iohexyl" and insert --iohexol--
In column 9, line 60, delete "iohexyl" and insert --iohexol--
In column 9, line 61, delete "iohexyl" and insert --iohexol--
In column 9, line 62, delete "iohexyl" and insert --iohexol--
In column 24, line 17, delete "iohexyl" and insert --iohexol--
In column 24, line 20, delete "iohexyl" and insert --iohexol--
In column 24, line 26, delete "iohexyl" and insert --iohexol--
In column 24, line 31, delete "iohexyl" and insert --iohexol--
In column 24, line 32, delete "iohexyl" and insert --iohexol--
In column 24, line 33, delete "iohexyl" and insert --iohexol--
In column 24, line 34, delete "iohexyl" and insert --iohexol--
In column 24, line 35, delete "iohexyl" and insert --iohexol--
In column 24, line 36, delete "iohexyl" and insert --iohexol--
In column 24, line 39, delete "iohexyl" and insert --iohexol--
In column 24, line 65, delete "iohexyl" and insert --iohexol--
In column 24, line 67, delete "iohexyl" and insert --iohexol--
In column 25, line 9, delete "iohexyl" and insert --iohexol--
In column 25, line 15, delete "iohexyl" and insert --iohexol--
In column 25, line 25, delete "iohexyl" and insert --iohexol--

In the Claims
In claim 1, column 26, line 26, delete "iohexyl" and insert --iohexol--
In claim 3, column 26, line 38, delete "iohexyl" and insert --iohexol--

Signed and Sealed this
Eleventh Day of February, 2014

Michelle K. Lee
*Deputy Director of the United States Patent and Trademark Office*